(12) United States Patent
Vetter et al.

(10) Patent No.: US 10,070,884 B2
(45) Date of Patent: Sep. 11, 2018

(54) SOFT TISSUE CORING BIOPSY DEVICES AND METHODS

(71) Applicant: TRANSMED7, LLC, Portola Valley, CA (US)

(72) Inventors: James W Vetter, Portola Valley, CA (US); Daniel E Clark, Riverside, CA (US); Eugene H Vetter, Portola Valley, CA (US); Alisen E Vetter, Shoreview, MN (US)

(73) Assignee: TransMed7, LLC, Portola Valley, CA (US)

( * ) Notice: Subject to any disclaimer, the term of this patent is extended or adjusted under 35 U.S.C. 154(b) by 432 days.

(21) Appl. No.: 14/491,348

(22) Filed: Sep. 19, 2014

(65) Prior Publication Data

US 2015/0133985 A1    May 14, 2015

Related U.S. Application Data

(62) Division of application No. 14/484,122, filed on Sep. 11, 2014.

(Continued)

(51) Int. Cl.
*A61B 10/00* (2006.01)
*A61B 17/3205* (2006.01)
(Continued)

(52) U.S. Cl.
CPC ...... *A61B 17/3205* (2013.01); *A61B 10/0266* (2013.01); *A61B 17/32002* (2013.01);
(Continued)

(58) Field of Classification Search
CPC ....... A61B 34/30; A61B 17/221; A61B 34/71; A61B 17/320758; A61B 2017/2215;
(Continued)

(56) References Cited

U.S. PATENT DOCUMENTS

| 1,493,240 A | 5/1924 | Bohn |
| 2,751,908 A | 6/1956 | Wallace |

(Continued)

FOREIGN PATENT DOCUMENTS

| CA | 2008190 | 7/1990 |
| CN | 101352357 | 1/2009 |
| CN | 102014842 | 4/2011 |

OTHER PUBLICATIONS

International Search Report dated Feb. 26, 2013 in related application PCT/US12/60149.

(Continued)

*Primary Examiner* — May Abouelela
(74) *Attorney, Agent, or Firm* — Young Law Firm, P.C.

(57) ABSTRACT

An excisional device for either handheld or stereotactic table/MRI use may comprise a work element configured to rotate at a first rotation rate and comprising at least one articulable beak configured to cut tissue in a longitudinal direction. Helical elements or equivalent assemblies may be configured to transport tissue cut by a work element and may be co-axially disposed relative to the work element and may be operative to rotate at rotation rates that may be different from the work element rotation rate. Flush and vacuum tissue transport mechanisms may be incorporated in replacement of or in conjunction with helical elements. A proximal sheath and a distal sheath may be co-axially disposed relative to a work element and may be configured to rotate a work element and to actuate a beak or beaks. A simplified embodiment of this device may be applicable to field use where power sources for actuation may be limited.

26 Claims, 16 Drawing Sheets

Related U.S. Application Data

(60) Provisional application No. 61/876,977, filed on Sep. 12, 2013.

(51) Int. Cl.
*A61B 10/02* (2006.01)
*A61B 17/32* (2006.01)
*A61B 17/00* (2006.01)

(52) U.S. Cl.
CPC ........... *A61B 2010/0208* (2013.01); *A61B 2010/0225* (2013.01); *A61B 2017/00473* (2013.01); *A61B 2017/320024* (2013.01); *A61B 2017/320028* (2013.01); *A61B 2017/320032* (2013.01); *A61B 2017/320064* (2013.01); *A61B 2217/007* (2013.01)

(58) Field of Classification Search
CPC ............ A61B 2034/302; A61B 17/30; A61B 2017/2212; A61B 2017/2906; A61B 90/57
USPC ................. 600/562, 564, 565, 566, 567
See application file for complete search history.

(56) References Cited

U.S. PATENT DOCUMENTS

| | | | |
|---|---|---|---|
| 3,175,554 A | 3/1965 | Stewart | |
| 3,913,566 A | 10/1975 | Lacey | |
| 4,522,206 A | 6/1985 | Whipple et al. | |
| 4,653,496 A | 3/1987 | Bundy et al. | |
| 4,682,606 A | 7/1987 | DeCaprio | |
| 4,781,186 A | 11/1988 | Simpson | |
| 5,052,402 A | 10/1991 | Bencini et al. | |
| 5,074,311 A | 12/1991 | Hasson | |
| 5,174,300 A | 12/1992 | Bales et al. | |
| 5,251,641 A | 10/1993 | Xavier | |
| 5,259,365 A | 11/1993 | Nishikori et al. | |
| 5,292,310 A | 3/1994 | Yoon | |
| 5,415,169 A | 5/1995 | Siczek et al. | |
| 5,507,296 A | 4/1996 | Bales et al. | |
| 5,526,822 A | 6/1996 | Burbank | |
| 5,573,008 A | 11/1996 | Robinson et al. | |
| 5,609,152 A | 3/1997 | Pellegrino et al. | |
| 5,636,639 A * | 6/1997 | Turturro | A61B 10/06 600/564 |
| 5,649,547 A | 7/1997 | Richart et al. | |
| 5,762,069 A | 6/1998 | Kelleher et al. | |
| 5,848,978 A | 12/1998 | Cecchi | |
| 5,871,453 A | 2/1999 | Banik et al. | |
| 5,873,886 A | 2/1999 | Larsen et al. | |
| 5,976,164 A | 11/1999 | Bencini et al. | |
| 6,083,237 A | 7/2000 | Huitema et al. | |
| 6,086,543 A | 7/2000 | Anderson et al. | |
| 6,139,508 A | 10/2000 | Simpson et al. | |
| 6,142,957 A | 11/2000 | Diamond et al. | |
| 6,149,607 A | 11/2000 | Simpson et al. | |
| 6,193,673 B1 | 2/2001 | Viola et al. | |
| 6,322,522 B1 | 11/2001 | Zimmon | |
| 6,383,145 B1 | 5/2002 | Worm et al. | |
| 6,391,043 B1 | 5/2002 | Moll et al. | |
| 6,409,742 B1 | 6/2002 | Fulton | |
| 6,447,525 B2 | 9/2002 | Follmer et al. | |
| 6,582,451 B1 | 6/2003 | Marucci et al. | |
| 6,599,309 B1 | 7/2003 | Gilman | |
| 6,632,182 B1 * | 10/2003 | Treat | A61B 10/06 600/564 |
| 7,008,381 B2 | 3/2006 | Janssens | |
| 7,641,667 B2 | 1/2010 | Sample | |
| 7,740,597 B2 | 6/2010 | Cicenas et al. | |
| 7,762,960 B2 | 7/2010 | Timberlake et al. | |
| 8,007,506 B2 | 8/2011 | To et al. | |
| 8,025,626 B2 * | 9/2011 | Freeman | A61B 10/06 600/562 |
| 8,037,591 B2 * | 10/2011 | Spivey | A61B 17/320016 29/525.01 |
| 8,114,072 B2 * | 2/2012 | Long | A61B 18/1492 606/37 |
| 8,118,755 B2 * | 2/2012 | Hibner | A61B 10/0275 600/562 |
| 8,157,834 B2 * | 4/2012 | Conlon | A61B 17/29 606/205 |
| 8,262,655 B2 * | 9/2012 | Ghabrial | A61B 18/1445 606/51 |
| 8,267,869 B2 * | 9/2012 | Lacombe | A61B 1/018 600/564 |
| 8,409,200 B2 * | 4/2013 | Holcomb | A61B 18/1445 606/51 |
| 8,568,410 B2 * | 10/2013 | Vakharia | A61B 18/1492 606/51 |
| 8,579,897 B2 * | 11/2013 | Vakharia | A61B 18/1445 606/207 |
| 8,603,135 B2 * | 12/2013 | Mueller | A61B 17/29 606/170 |
| 8,936,557 B2 | 11/2015 | Al-Mohizea | |
| 2001/0034495 A1 | 10/2001 | Wilson et al. | |
| 2002/0165580 A1 | 11/2002 | Zwiefel et al. | |
| 2003/0032955 A1 | 2/2003 | Mulier | |
| 2003/0114773 A1 | 6/2003 | Janssens | |
| 2004/0073139 A1 | 4/2004 | Hirsch et al. | |
| 2005/0049520 A1 * | 3/2005 | Nakao | A61B 10/06 600/562 |
| 2005/0070885 A1 | 3/2005 | Nobis et al. | |
| 2005/0209564 A1 | 9/2005 | Bonner et al. | |
| 2006/0258955 A1 | 11/2006 | Hoffman | |
| 2007/0167868 A1 * | 7/2007 | Sauer | A61B 10/0233 600/564 |
| 2007/0219459 A1 | 9/2007 | Cohen | |
| 2007/0255311 A1 | 11/2007 | Hiraoka | |
| 2007/0270712 A1 | 11/2007 | Wiksell et al. | |
| 2008/0045860 A1 | 2/2008 | Miller et al. | |
| 2008/0221480 A1 | 9/2008 | Hibner et al. | |
| 2009/0204023 A1 | 8/2009 | Goldenburg | |
| 2009/0264910 A1 | 10/2009 | Laufer | |
| 2009/0287114 A1 | 11/2009 | Lee et al. | |
| 2009/0299220 A1 | 12/2009 | Field et al. | |
| 2009/0318830 A1 * | 12/2009 | George | A61B 10/0291 600/564 |
| 2010/0078296 A1 | 4/2010 | Lapeyre et al. | |
| 2010/0121153 A1 | 5/2010 | To | |
| 2010/0312141 A1 | 12/2010 | Keast et al. | |
| 2011/0125054 A1 | 5/2011 | Clements et al. | |
| 2011/0132961 A1 | 6/2011 | Whitman et al. | |
| 2011/0213360 A1 | 9/2011 | Cunningham | |
| 2011/0245716 A1 | 10/2011 | Flatland et al. | |
| 2011/0245725 A1 | 10/2011 | Flatland et al. | |
| 2011/0288437 A1 | 11/2011 | Ryan | |
| 2012/0209140 A1 * | 8/2012 | Ryan | A61B 10/06 600/564 |
| 2013/0041256 A1 | 2/2013 | Flebig | |
| 2013/0096459 A1 | 4/2013 | Vetter | |
| 2013/0190651 A1 | 7/2013 | Vetter | |
| 2014/0142602 A1 | 5/2014 | Polo | |
| 2014/0213932 A1 | 7/2014 | Knoll et al. | |

OTHER PUBLICATIONS

Written Opinion of the International Searching Authority dated Feb. 26, 2013 in related application PCT/US12/60149.
USPTO Office Action dated Jan. 16, 2015 is related U.S. Appl. No. 13/651,393.
USPTO Office Action dated Jun. 19, 2015 in related U.S. Appl. No. 13/853,719.
USPTO Office Action dated Apr. 13, 2015 in related U.S. Appl. No. 13/853,768.
USPTO Office Action dated Feb. 3, 2015 in related U.S. Appl. No. 13/973,898.
USPTO Office Action dated Apr. 10, 2015 in related U.S. Appl. No. 13/853,636.

(56) References Cited

OTHER PUBLICATIONS

International Search Report and Written Opinion of International Searching Authority dated Apr. 16, 2015 in related PCT application PCT/US14/51945.
European Patent Office Extended Search Report dated Mar. 20, 2015 in related EP patent application 12839250.3.
International Search Report and Written Opinion of International Searching Authority dated Mar. 11, 2015 in related PCT application PCT/US14/55190.
International Search Report and Written Opinion of International Searching Authority dated Mar. 23, 2015 in related PCT application PCT/US14/39676.
International Search Report and Written Opinion of International Searching Authority dated Apr. 23, 2015 in related PCT application PCT/US14/39688.
USPTO Office Action dated Apr. 10, 2015 in related U.S. Appl. No. 13/853,837.
USPTO Office Action dated May 5, 2015 in related U.S. Appl. No. 13/973,898.
International Search Report and Written Opinion in PCT/US15/50868, dated Dec. 18, 2015.
USPTO Office Action dated Oct. 16, 2015 in U.S. Appl. No. 14/052,727.
USPTO Office Action dated Oct. 9, 2015 in U.S. Appl. No. 14/853,806.
International Search Report and Written Opinion in PCT/US14/039676, dated Apr. 23, 2015.
International Search Report and Written Opinion in PCT/US14/039688, dated Apr. 23, 2015.
USPTO Office Action dated Oct. 30, 2015 in U.S. Appl. No. 13/903,800.
USPTO Office Action dated Apr. 10, 2015 in related U.S. Appl. No. 13/651,393.
USPTO Office Action dated Jul. 1, 2015 in related U.S. Appl. No. 13/853,806.
USPTO Office Action dated Sep. 25, 2015 in U.S. Appl. No. 13/651,393.
USPTO Office Action dated Sep. 25, 2015 in U.S. Appl. No. 13/853,636.
USPTO Office Action dated Sep. 29, 2015 in U.S. Appl. No. 13/853,719.
USPTO Office Action dated Sep. 25, 2015 in U.S. Appl. No. 13/853,768.
USPTO Office Action dated Jul. 1, 2015 in U.S. Appl. No. 13/853,806.
USPTO Office Action dated Jul. 17, 2015 in U.S. Appl. No. 13/903,800.
USPTO Office Action dated Jul. 15, 2015 in U.S. Appl. No. 13/903,833.
USPTO Notice of Allowance dated Jul. 16, 2015 in U.S. Appl. No. 13/973,898.
USPTO Office Action dated Aug. 21, 2015 in U.S. Appl. No. 14/050,771.
USPTO Office Action dated Sep. 25, 2015 in U.S. Appl. No. 14/050,885.
CIPO Office Action dated Jun. 11, 2015 in CN Application No. or Patent No. 201280060967.8 Serial No. 2015060801263610.

* cited by examiner

SOFT TISSUE CORING BIOPSY DEVICES AND METHODS

RELATED CASES

The present patent application is a Divisional of commonly assigned and co-pending US patent application Ser. No. 14/484122 tiled on Sep. 11, 2014, the disclosure of which is incorporated herein by reference in its entirety.

BACKGROUND

Embodiments relate to medical devices and methods. More particularly, embodiments relate to hand held or mounted single insertion, multiple sample tissue biopsy and coring devices and corresponding methods for retrieving multiple pieces of tissue using a single insertion.

SUMMARY

Embodiments are drawn to various medical devices and methods that are used for core biopsy procedures. According to one embodiment, a biopsy coring/delivery device, also referred to herein as an excisional device, may be configured to retrieve multiple samples of normal and/or abnormal appearing biological tissues or other materials during a single insertion through the skin (percutaneous procedure) into the, for example, soft or hard tissue area of the body from which the biopsy is taken. Embodiments may comprise structures and functionality for different phases of a multi-phase biopsy procedure, which may be performed by hand or by attachment to a stereotactic table stage or Magnetic Resonance Imaging (MRI) stage. For example, embodiments may comprise a pre-treatment of the area and/or of the abnormal tissue, or the delivery of tracer materials for tracking the potential spread or flow patterns whereby the abnormal tissues (such as cancerous tissues) may metastasize. Embodiments may also comprise an intra-procedure delivery of medications that may anesthetize tissues at the site, or the delivery of other therapeutic agents such as pro-coagulants and others, as well as delivery of post-procedure materials such as medications, implantable materials for cosmetic purposes and other implantable elements such as marking devices for later imaging reference. Embodiments of a biopsy device, along with associated related subcomponents described herein, may provide the capability to retrieve solid, contiguous and/or fragmented tissues as well as liquid and semi-solid tissues for analysis, diagnosis and treatment. Embodiments may be configured to be portable, disposable or reusable and may be, for example, electrically-, mechanically-, hydraulic-, pneumatic- and/or manually-powered and operated.

Accordingly, one embodiment is an excisional device, may comprise a handle portion may comprise a distal end and a proximal end; a cutting assembly coupled to the distal end of the handle portion and may be configured to rotate, core and part-off pieces of tissue; a tissue storing magazine coupled to the proximal end of the handle portion and may be configured to receive and store the parted-off pieces of tissue; and a transport assembly disposed at least partially within the handle portion and may be configured to receive the parted-off pieces of tissue and transport them toward the tissue storing magazine. The cutting assembly may be configured, during a single insertion thereof into tissue, to rotate, core and part-off pieces of tissue while the transport assembly transports the parted-off pieces of tissue and while the tissue storing magazine receives and stores the transported pieces of tissue.

The device may be configured, in an automatic mode of operation, to cyclically core, part-off, transport and store same-length pieces of tissue. In a semi-automatic mode of operation, the device may be configured to core, part-off, transport and store a single piece of tissue each time an actuator on the handle portion is actuated. The device may be configured, in a manual mode of operation, to core and part-off one or more pieces of tissue of selectable length upon actuation of a manual part-off mechanism on the handle portion. The device may be configured to part-off pieces of tissue at a selectable rate. The device may be configured to part-off pieces of tissue having a selectable length. The cutting assembly may comprise one or more beaks articulable via a living hinge. The beak(s) may be configured to selectively assume an open configuration suitable for coring and a closed configuration suitable for parting-off tissue, tissue penetration and/or for tissue dissection. The cutting assembly may be configured to move, while coring, in a distal direction over a selectable excursion distance. The cutting assembly comprises one or more hypo tubes in which cuts are selectively made to form at least one (i.e., one or more) articulable cutting elements. The articulable cutting element(s) may be electively actuable to assume an open configuration and a closed configuration.

Another embodiment is a method of excising tissue, comprising providing an excisional device that may comprise a handle portion, a cutting assembly coupled to one end of the handle portion and may be configured to rotate, penetrate, core and part-off tissue; a tissue storing magazine coupled to another end of the handle portion and may be configured to receive and store the parted-off tissue, and a transport assembly disposed at least partially within the handle portion and may be configured to receive the parted-off tissue and transport them toward the tissue storing magazine; and carrying out a single insertion of at least the cutting assembly into tissue and, during the single insertion, rotating the cutting assembly, penetrating the tissue, coring through the tissue and parting-off at least one piece of tissue using the rotating cutting assembly, while the transport assembly transports parted-off tissue toward the tissue storing magazine and while the tissue storing magazine receives and stores the transported tissue. The method may further comprise operating the excisional device in an automatic mode of operation, to repeatedly core, part-off, transport and store same-length pieces of tissue. The method may also comprise operating the excisional device in a semi-automatic mode of operation, to core, part-off, transport and store a single piece of tissue each time an actuator on the handle portion is actuated. The method may also comprise operating the excisional device in a manual mode of operation, to penetrate, core and part-off one or more pieces of tissue of selectable length upon actuation of a manual part-off mechanism on the handle portion. The method may also comprise parting-off tissue at a selectable rate. The method may also comprise parting-off pieces of tissue having an operator-selectable length. The cutting assembly may comprise at least one articulable beak configured to selectively assume an open configuration suitable for coring and a closed configuration suitable for parting-off tissue, tissue penetration and/or for tissue dissection. The method may also comprise moving the cutting assembly over a selectable excursion distance during the single insertion. The cutting assembly may comprise a single hypo tube in which cuts are selectively made to form the articulable cutting element(s). The cutting assembly may be selectively actuable to assume an open configuration and a closed configuration.

Another embodiment is an excisional device, which may comprise a handle portion may comprise a distal end and a proximal end; a cutting assembly coupled to the distal end of the handle portion and may be configured to rotate, penetrate, core, part-off and transporting and/or containing parted-off tissue; and a tissue storing magazine coupled to the proximal end of the handle portion and configured to receive and store the parted-off tissue. The cutting assembly may be configured to rotate, core and part-off pieces of tissue of a length determined by an amount of forward excursion of the cutting assembly within tissue before the cutting assembly parts-off the tissue sample.

The parted-off tissue contained in the cutting assembly may be configured to be pushed into the tissue storing magazine by a push rod inserted axially within the cutting assembly. The device may further comprise manual part-off actuator, configured to cause the cutting assembly to part-off cored tissue from surrounding tissue. The cutting assembly may be configured to rotate under power from a mechanical wind-up motor within the handle portion. Alternatively or in addition, the cutting assembly may be configured to rotate under power from an electrical motor within the handle portion. The cutting assembly may comprise at least one (i.e., one or more) articulable beaks configured to selectively assume an open configuration suitable for coring and a closed configuration suitable for parting-off pieces of tissue, penetrating tissue and/or for tissue dissection. The cutting assembly may comprise a single hypo tube in which cuts are selectively made to form at least one articulable cutting element. The articulable cutting element(s) may be electively actuable to assume an open configuration and a closed configuration. The handle portion may comprise a lower portion and a detachable upper portion. The detachable upper portion may be pivotably coupled to the lower portion. The cutting assembly may be detachable from the handle portion. The tissue storing magazine may be detachable from the handle portion. The device may further comprise a flush port through which liquids (for example) may be delivered and evacuated.

A further embodiment is a method of excising tissue, which may comprise providing an excisional device may comprise a handle portion; a cutting assembly coupled to one end of the handle portion and may be configured to rotate, penetrate, core, part-off and transport or contain parted-off tissue and a tissue storing magazine coupled to another end of the handle portion and configured to receive and store the parted-off tissue. At least the cutting assembly of the provided excisional device may then be inserted into tissue. The method may also comprise rotating the cutting assembly; advancing the cutting assembly within the tissue while coring, and creating pieces of tissue of a length determined by a distance the cutting assembly advanced within the tissue before being parted-off by the cutting assembly.

The method may further comprise axially inserting and pushing a push rod within the cutting assembly to push the parted-off pieces of tissue contained in the cutting assembly into the tissue storing magazine. The method may further comprise actuating a manual part-off actuator configured to cause the cutting assembly to part-off cored tissue from surrounding tissue. The method may further comprise winding up a mechanical wind-up motor within the handle portion to power the cutting assembly. The method may further comprise applying electrical energy to an electrical motor within the handle portion to power at least the cutting assembly. The providing step may be carried out with the cutting assembly comprising one or more articulable beaks configured to selectively assume an open configuration suitable for coring and a closed configuration suitable for parting-off tissue and/or penetrating tissue. The providing step may be carried out with the cutting assembly comprising single hypo tube in which cuts are selectively made to form one or more articulable cutting elements. The providing step may be carried out with the articulable cutting element(s) being selectively actuable to assume an open configuration and a closed configuration.

The providing step may be carried out with the handle portion comprising a lower portion and a detachable upper portion. The providing step may be carried out with the detachable upper portion being pivotably coupled to the lower portion. The method may further comprise detaching the cutting assembly from the handle portion after the pieces of tissue are created. The method may further comprise detaching the tissue storing magazine, with the tissue stored therein, from the handle portion. The method may further comprise delivering or evacuating a liquid through a flush port provided in the handle portion.

A still further embodiment is an excisional device, comprising a handle portion may comprise a distal end and a proximal end; an articulable beak assembly that may be configured to rotate, core through tissue and part-off pieces of tissue from surrounding tissue; a proximal sheath, coupled to the articulable beak assembly, which may be configured to both rotate and move in axial proximal and distal directions; a distal sheath fitted at least partially over the proximal sheath that may be configured to both rotate and move in the axial proximal and distal directions independently of the proximal sheath. According to one embodiment, differential axial movement of the proximal sheath relative to the distal sheath opens and closes the beak assembly.

The device may further comprise a twin gear cam and cam elements within the handle portion, which collectively may be configured to differentially drive respective movements of the proximal sheath and of the distal sheath. The device may further comprise a first carrier coupled to the distal sheath and a second carrier coupled to the proximal sheath. The distal and proximal sheaths may be configured to slide in the axial proximal direction and in the axial distal direction in response to respective axial movement of the first and second carriers. Each of the first and second carriers may be resiliently biased toward the proximal end of the handle portion. An axial distance over which the proximal carrier slides may be related to a length of the pieces of tissue parted-off by the beak assembly. The beak assembly, the proximal sheath and the distal sheath may be configured and/or operated to penetrate tissue with the beak assembly in an open or closed configuration while rotating or not rotating; carry out semi-automatic tissue parting-off or fully automatic tissue parting-off; and/or manually part-off pieces of tissue of manually selectable lengths. The device may further comprise a transport assembly disposed at least partially within the handle portion and may be configured to receive the parted-off pieces of tissue and transport them in a proximal direction. The device may further comprise a tissue storing magazine coupled to the proximal end of the handle portion, which may be configured to receive and store the parted-off pieces of tissue transported by the transport assembly. The cutting assembly may be configured, during a single insertion thereof into tissue, to rotate, core and part-off tissue while the transport assembly transports the parted-off tissue and while the tissue storing magazine receives and stores the transported tissue. The device may be configured, in an automatic mode of operation, to repeatedly part-off transport and store same-length pieces of tissue. Alternatively, the device may be configured, in a semi-automatic mode of operation, to part-off, transport and store a single piece of tissue each time an actuator on the handle portion is actuated. The device may be configured, in a manual mode of operation, to part-off one or more pieces of tissue of selectable length upon actuation of a manual part-off mechanism on the handle portion. The device may be configured to part-off tissue at a selectable rate. The device may be configured to part-off pieces of tissue having a selectable length. The articulable beak assembly may be configured to selectively assume an open configuration suitable for coring and a closed configuration suitable for parting-off tissue, tissue penetration and/or for tissue dissection. The articulable beak assembly may be configured to move, while coring, in a distal direction by a selectable excursion distance. The articulable beak may comprise single hypo tube in which cuts are selectively made to form at least one articulable cutting elements.

The device may further comprise a gear cam driven in rotation with the handle portion; a first pin disposed against the rotating gear cam gear and may be configured to act upon the proximal sheath, and a second pin configured disposed away from the first pin against the rotating cam gear and may be configured to act upon both the proximal sheath and the distal sheath to drive the distal and proximal movement of the proximal sheath and of the distal sheath.

The first and second pins may be configured to be driven against the rotating gear cam together or in a lead/lag relationship. The time between successive pieces of tissue parted-off from surrounding tissue may be related to the speed of rotation of the gear cam. The axial distance between the first and second pins may be related to the length of pieces of tissue parted-off by the articulable beak assembly.

Yet another embodiment is a method of excising tissue, comprising providing an excisional device comprising a handle portion, an articulable beak assembly, a proximal sheath coupled to the beak assembly and a distal sheath fitted at least partially over the proximal sheath; inserting at least the articulable beak assembly into tissue; rotating the articulable beak assembly; and differentially moving the proximal sheath relative to the distal sheath to selectively open the articulable beak assembly to core through tissue and to close the articulable beak assembly to part-off cored tissue from surrounding tissue.

The providing step may be carried out with the proximal sheath being configured to both rotate and move axially in proximal and distal directions. The providing step may be carried out with the distal sheath being configured to both rotate and move axially in the axial proximal and distal directions independently of the proximal sheath. The providing step may be carried out with the excisional device further comprising a twin gear cam and cam elements within the handle portion, which may be configured to differentially drive respective movements of the proximal sheath and of the distal sheath. The providing step may be carried out with the excisional device further comprising a first carrier coupled to the distal sheath and a second carrier coupled to the proximal sheath. The distal and proximal sheaths may be configured to slide in the axial proximal direction and in the axial distal direction in response to respective axial movement of the first and second carriers. Each of the first and second carriers may be being resiliently biased toward the proximal end of the handle portion. An axial distance over which the proximal carrier slides may be related to the length of the pieces of tissue parted-off by the articulable beak assembly. The method may further comprise operating the articulable beak assembly, the proximal sheath and the distal sheath to penetrate tissue with the articulable beak assembly in an open or closed configuration while rotating or not rotating; carry out semi-automatic tissue parting-off or fully automatic tissue parting-off; and/or manually part-off pieces of tissue of manually selectable lengths. The method may further comprise providing a transport assembly at least partially within the handle portion. The transport assembly may be configured to receive the parted-off pieces of tissue and transport them in a proximal direction. The method may further comprise providing a tissue storing magazine coupled to the proximal end of the handle portion, which may be configured to receive and store the parted-off pieces of tissue transported by the transport assembly. The method may comprise, during a single insertion of the articulable cutting assembly into the tissue, rotating the articulable cutting assembly, coring tissue and parting-off pieces of tissue from the cored tissue, transporting the parted-off pieces of tissue in the transport assembly, and/or receiving and storing the transported pieces of tissue in the tissue storing magazine. Rotating, coring, transporting and/or receiving and storing are carried out simultaneously. The method may comprise operating the excisional device in an automatic mode of operation in which same-length pieces of tissue are cyclically parted-off, transported and stored. The method may comprise operating the excisional device a semi-automatic mode of operation in which a single piece of tissue is parted-off, transported and stored each time an actuator on the handle portion is actuated. The method may comprise operating the excisional device in a manual mode of operation in which one or more pieces of tissue of selectable length are parted-off upon actuation of a manual part-off mechanism on the handle portion. The method may further comprise parting-off pieces of tissue at a selectable rate. The method may further comprise selecting the length of parted-off pieces of tissue. The excisional device may be provided with the articulable beak assembly configured to selectively assume an open configuration suitable for coring and a closed configuration suitable for at least one of parting-off pieces of tissue and for tissue dissection. The method may further comprise moving the articulable beak assembly, while coring, in a distal direction by a selectable excursion distance. The excisional device may be provided with the articulable beak may comprise single hypo tube in which cuts are selectively made to form at least one articulable cutting elements.

The excisional device may be provided with a gear cam driven in rotation with the handle portion and a first pin disposed against the rotating gear cam gear and configured to act upon the proximal sheath and a second pin configured disposed away from the first pin against the rotating cam gear and to act upon both the proximal sheath and the distal sheath to drive the distal and proximal movement of the proximal sheath and of the distal sheath. The method may further comprise driving the first and second pins against the rotating gear cam together or in a lead/lag relationship. The method may further comprise configuring the speed of rotation of the gear cam to be related to a time between successive pieces of tissue parted-off from surrounding tissue. The method may further comprise configuring an axial distance between the first and second pins to be related to a length of pieces of tissue parted-off by the articulable beak assembly.

DETAILED DESCRIPTION

Figure 1:
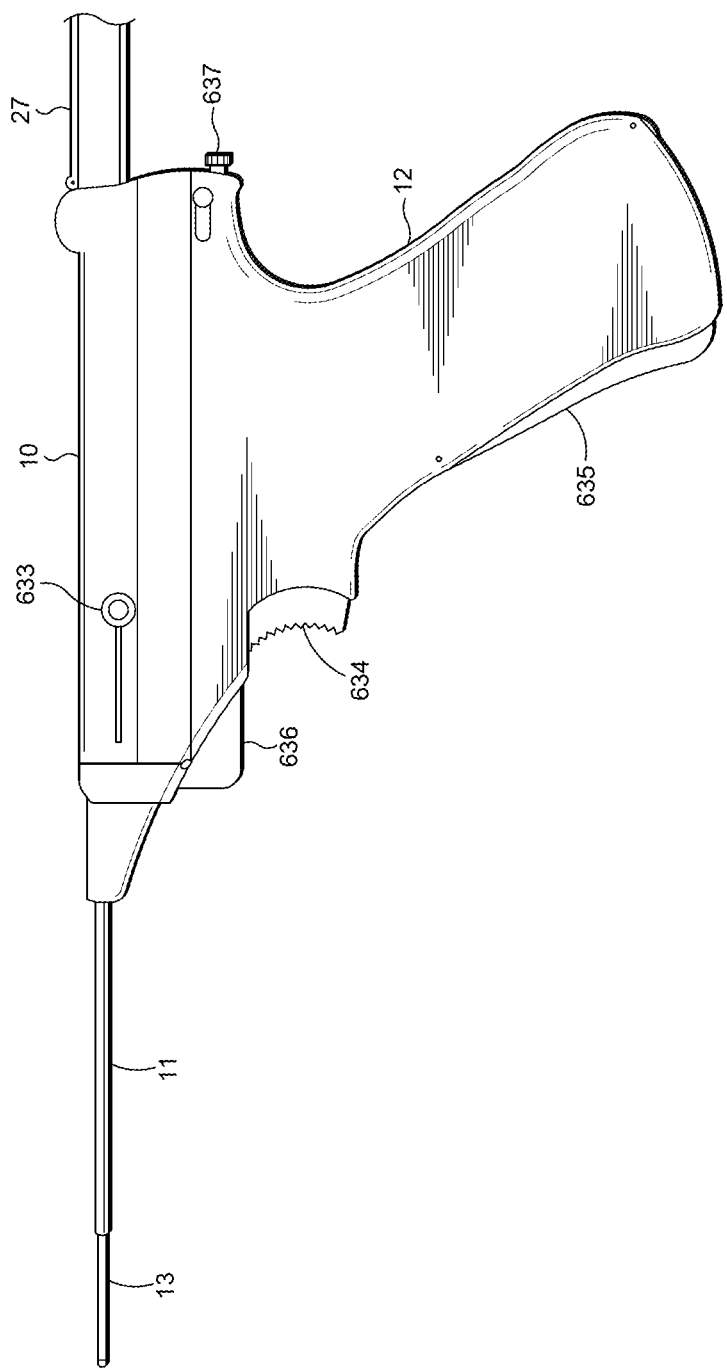
FIG. 1 is a perspective view of a core biopsy device according to embodiments.

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations.

Core biopsy procedures have evolved from simple core needle biopsies comprising aspiration of fluids using a simple syringe and needle to devices having the capability to extract solid tissues for histopathological analysis. This more recent capability has proved to be a far more powerful way to diagnose diseases and abnormal tissue entities, some of which are extremely life threatening, and others which may be more benign but nevertheless must be definitively distinguished from the more dangerous types of abnormalities, including cancerous and pre-cancerous lesions, in-situ cancers, invasive cancers, benign space occupying lesions, cystic lesions and others. As core biopsy procedures have evolved into far more diagnostically powerful tools, they have displaced many of the more invasive open surgical procedures, which had been and continue to be performed for diagnostic purposes. One of the most critical needs during a biopsy procedure is to accurately correlate tissue diagnosis with imaging diagnosis. In order to successfully accomplish this, it is essential to know that the retrieved tissue actually and accurately represents the imaged abnormality. This is an aspect where many conventional coring devices fall short, and for this reason, open surgical diagnostic procedures and other invasive procedures continue to be performed. Other clinically significant limitations of conventional coring devices include the manner in which the abnormal tissue is separated from the host organ, the manner in which the tissue is retrieved and handled during the process by the coring biopsy device, and the amount of biopsy artifact/damage imparted to the tissue specimens by the coring procedure and device. It is well known that the larger the caliber of the retrieved tissue samples, the better the correlation with the imaging abnormality, and thus the easier, more accurate, definitive and helpful the diagnosis. However, in order to retrieve larger caliber specimens, most biopsy devices have large outer diameters, leading to increased trauma, complications, pain and other adverse effects, due principally to the imprecision associated with such large bore devices. Additionally, moving a large bore device through the tissues is much more difficult, particularly without the help of an active mechanism to aid in smoother and more gradual advancement of the biopsy device. The larger the caliber of the biopsy device, the more difficult it becomes to precisely visualize the biopsy device in relation to the target abnormality, especially for small lesions (on the order of about ½ cm to less than ¼ cm). Today, more than 4-5 million diagnostic core biopsies are performed each year around the world in the breast alone, with as many as 2 million diagnostic breast biopsies being performed each year in the US. There is little doubt that many invasive, open surgical diagnostic biopsies should be replaced by improved core biopsy procedures.

Reference will now be made in detail to the construction and operation of preferred implementations illustrated in the accompanying drawings. FIG. 1 shows a biopsy or, more generally, an excisional device 10 according to embodiments, having a tubular coring and transport assembly 11 (also called an "outer tube," "distal sheath," "non- or differentially-rotating outer sheath" or "outer sheath" herein, depending on embodiments) of appropriate dimensions to retrieve a single or multiple core samples of tissue (not shown) that is or are sufficient to provide the desired clinical diagnostic or therapeutic result. Such an appropriate dimension may be, for example, about 6 inches in length, in addition to a forward excursion of a tubular coring and transport assembly 11 during the coring phase. It is to be understood, however, that the foregoing dimensions and any dimensions referred to herein are exemplary in nature only and are not limiting factors. Those of skill in this art will recognize that other dimensions and/or configurations may be implemented, depending upon the application, and that a tubular coring assembly and its subparts could be of any length.

One embodiment of the biopsy device 10, as shown in the figures, may be implemented in a hand-held configuration comprising an ergonomically comfortable and secure handle portion 12 at its proximal end from which a tubular coring and transport assembly 11 extends so that the biopsy device 10 may be easily directed with one hand while the other hand is free to hold a guiding probe such as an ultrasound transducer. However, it is to be understood that embodiments may readily be configured to fit onto any number of guiding devices such as a stereotactic imaging stage or other guidance modality such as MRI (not shown). As shown, one embodiment of the biopsy device 10 may comprise one or more sharp, rotating cutting elements 13 (herein, alternatively and collectively referred to as "work element", "beak", "beak assembly" or "beak element" or "beak elements") projecting forward distally from the distal free end of the tubular coring and transport assembly 11 for the purpose of forward penetration, coring and parting off of a cored sample in a simple point and shoot procedure. A tubular coring and transport assembly 11 may comprise a plurality of components, which plurality may be configured to transmit rotational movement to rotating or non-rotating cutting elements 13. It is to be understood that the "tubular" description of a coring and transport assembly may be of any cross section shape and size, of any length. The components of a tubular coring and transport assembly 11 also transfer a core sample (or piece of tissue, the present device not being limited to biopsy applications) back proximally along the internal length of an inner lumen of a tubular coring and transport assembly 11 to a handle portion 12 and storage compartment or a transfer magazine 27. According to one embodiment thereof, the biopsy device 10 may comprise handle portion 12, which handle portion 12 may comprise and/or be coupled to mechanical components (not shown in this figure) needed to drive a coring/transport/part-off delivery distal tubular coring and transport assembly 11. As shown, one embodiment may comprise a distally-disposed beak 13 that may comprise one or more sharp cutting tip blades to penetrate to the target site of the intended biopsy, core the target tissue and part-off or cut off a core sample (not shown) at its base or at any desired point along the length of a core sampling. The ability of the present biopsy device to repeatedly core and retrieve multiple samples (not shown) during a single insertion and then store the cored samples in a transfer magazine 27 means that with a single penetration through the skin of, for example, a human breast, the operator can sample multiple areas without causing additional trauma that would be associated with having to remove the biopsy device 10 each time a sample is taken, and reintroducing the biopsy device 10 back into the patient to take additional core samples. A handle portion 12 may also contain and/or be coupled to (internal or external) mechanical components (not shown) for vacuum-assisted fluid evacuation as well as the delivery of materials such as, for example, a variety of flushes, medications, tracer materials and/or implantable marker elements (not shown). A distal tubular coring and transport assembly 11, according to one embodiment, may be configured such as to create the smallest possible caliber (e.g., diameter) of coring tube (tubular coring and transport assembly 11) with a range of (for example) about 16 gauge or 0.65 inches in diameter to about 1 inch or more diameter, while providing a sufficiently large diameter of core sample to be clinically useful. A tubular coring and transport assembly 11 may also be constructed of flexible materials and/or of a sufficient length to reach distant target sites from the skin surface without the need for a surgical procedure to enable the distal end (that end thereof that is furthest from a handle portion 12) of the biopsy device 10 to reach the targeted site. In the embodiment of FIG. 1, a distal tubular coring and transport assembly 11 of the biopsy device 10 may extend distally from a handle portion 12 to a distance sufficient to create a tissue core (not shown) for diagnosis and/or treatment purposes. As is described below, this distance of forward or distal projection can be selectively changed at will, thanks to structure configured for that purpose, which may be built into or otherwise coupled to the present biopsy device 10. Embodiments of the present biopsy device 10 may be used by right and/or left handed persons and in multiple positions and orientations so that in areas of limited access the present biopsy device may still be easily positioned for ideal orientation to perform a biopsy procedure under real time or other image guidance (not shown). The entire device may be configured to be disposable or may be configured to be reusable in whole or in part. Embodiments of the present biopsy device 10 may be electrically powered by one or more batteries (not shown in this figure) and/or external power sources (not shown in this figure) through a simple electrical coupling to connect to an external power supply conveniently placed, for example, in a handle portion or proximal end of the present biopsy device. The entire device may also be internally or externally manually powered, mechanically powered or be powered by means such as compressed air, gas or pressurized fluid. Powering the biopsy device entirely mechanically may be advantageous in areas in which the electric grid is absent, unavailable, or unreliable. In FIG. 1, the biopsy device 10 is shown in a pre-coring configuration with the distal end thereof closed and in a configuration in which it may be partially projecting forward from its resting position from a proximal handle portion 12. FIG. 1 also shows illustrative placement of various external controls such as manual part off lever 633, and cam clutch button 634, as well as other features such as power switch/led indicator 635, motor 636 and DC power plug 637. The placement of these features is illustrative in nature and embodiments may contain some or all of these features in various locations.

According to one embodiment, a method of carrying out a biopsy procedure may comprise the following example, based on breast biopsy procedures which ordinarily begin with imaging the tissue of the organ (such as the breast) of interest and identifying the target lesion(s) or tissue to be removed. The skin may then be cleansed using sterile techniques, and the patient may be draped and anesthetics may be delivered. The distal tip of the present biopsy device may then be introduced through a skin nick incision. Further still, a guiding element could be coaxial with, in tandem with or adjacent to the long axis of elements of the biopsy device. A guiding element could additionally be a completely separable entity, such as a removable outer sheath that may function as a locating tube, which may be pre-placed by an operator skilled in imaging and targeting and fixed in place near or within the target tissue. After placement and fixation an operator may then proceed by advancing the biopsy instrument over a previously precisely placed and anchored guiding element.

The biopsy device may be advanced percutaneously to the target tissue site and fluids or anesthetics may be delivered during that process. An optional delivery stage may also be initiated, to deliver, for example, the contents of a preloaded cartridge such as tracer elements like visible dyes, echoenhancing materials and/or radioactive tracer elements, or others, for example, medications such as epinephrine or anesthetics which may be delivered at any stage of the biopsy procedure either directly through open beaks, through living hinges of closed beaks or via a reverse flow from a flush system built into the device. Tissue samples may then be taken in manual, automatic or semi-automatic modes. If short samples or very long samples are desired, the operator may manually part off the sample to be taken at any length of the forward movement of cutting elements and/or the device itself. Fluid flushes containing material from the tissue site may be collected by aspiration for later cytological analysis. During one or more of the corings, a record stage may be activated to halt a coring stage just after the specimen has been parted-off in order to enable the practitioner to record image(s) of the shaft of the biopsy device in place in the lesion, and to document that core samples (particularly those of different chosen lengths obtained serially during the procedure) were acquired precisely from imaged lesions or in precise locations within imaged lesions. A removable magazine 27 may be placed into a receptacle that may be preloaded with fluid such as, for example, sterile saline or preservative, and then such receptacle may be sealed. A specimen ultrasound or a radiograph may be carried out upon the specimens collected within a transfer magazine 27, which may be especially configured for echo and radio-lucency as well as compatibility with MRI and other imaging technologies. If desired, a replacement magazine 27 may be loaded into the device to continue the biopsy. An adapter for delivery of aforementioned materials to the biopsy site may be substituted for a magazine 27 at any time. Following the acquisition of a sufficient number of core samples and following the documentation stage, the core sample acquisition site may be firmly correlated with the image abnormality location. With the biopsy device 10 still in place, a tissue transfer magazine 27 may be replaced with an injection cartridge (not shown) that may be pre-loaded with intra-procedure and/or post-procedure elements, for example, medications, cosmetic implants, brachytherapy elements such as a radio-active seed, or a porous element loaded with a biologically active substance and other materials. A replacement transfer magazine 27 may be removed at the end of the procedure. A removable transfer magazine 27 may then be placed into a receptacle that may be preloaded with fluid such as, for example, sterile saline or preservative, and such receptacle may be sealed. The present biopsy device may then be removed from the site and the wound may be dressed, with the usual standard of care procedures. Alternatively, the biopsy device 10 may be withdrawn from a removable outer sheath, present according to embodiments, which outer sheath may then be used for delivery of post-procedure materials to the target site while other components of the biopsy device may be packaged appropriately and delivered to an appropriate laboratory for pathology/cytology analysis. An outer sheath of the biopsy device may then be completely removed from the site and the wound dressed using the customary standard of care procedures. If so attached to biopsy device 10 via an aspiration/material delivery port 639, a liquid aspirate collection vessel may be removed from biopsy device 10 at any time and capped securely for transport to an appropriate laboratory for cellular and subcellular analysis.

It is to be understood that the above description is but one exemplary methodology and that one or more of the steps described above may be omitted, while other steps may be added thereto, depending on the target site within the body, which is not limited to the breast, or other operator methodologies. The order of some of the steps may be changed, according to the procedure.

Turning now to further embodiments and in more detail, the discussion that follows will focus on general features of a whole device 10, which may comprise a distal end consisting of an outer sheath, a distal sheath, a proximal sheath, work element or elements and may also comprise first, second and third helical elements, in any combination or combinations of the above according to embodiments, as well as other elements such as suggested by FIG. 1 and as detailed further below, starting from the distal end and continuing to the proximal end of a device 10.

Figure 2A:
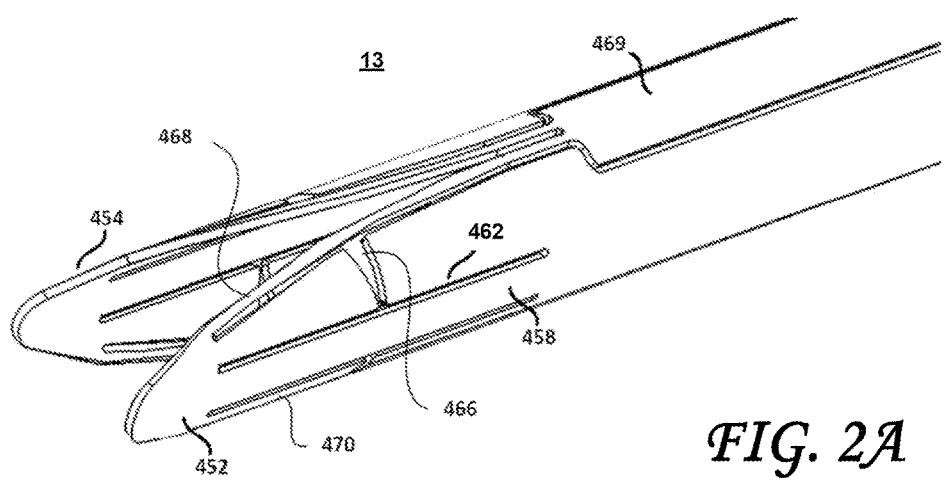
FIGS. 2A and 2B show details of a work element and FIG. 2B additionally shows details of an outer or distal sheath of an excisional device according to one embodiment.

FIG. 2A shows that a first, or according to embodiments, first and second or more articulable beaks (one of which may be fixed or rigid or non-articulable, according to embodiments) may comprise one or more slots 462 therein to form a living hinge 458. Additionally, wedge-shaped (for example) cutouts 466, which may be left joined at the base of a wedge adjacent to slots 462, may be provided to define an articulable beak(s) of a work element 13, improve the articulation thereof and provide for a greater range of motion. These living hinges may also serve as conduits for medications (anesthetics and epinephrine, for example) and other liquids, for example, saline flushes, to flow through a central lumen of the device for delivery to the distal end of the device 10, even if such beak(s) may be closed during such an intra-operative procedure. According to embodiments, each of a first and second articulable beak tips 452, 454 may define a first tendon 468 coupled to one side of a first articulable beak and a second tendon 470 coupled to the other side of a first articulable beak. Alternatively, a single tendon may be defined or multiple tendons may be defined. Additionally, these tendons may be defined at different relative angles to each other to impose an unequal or asymmetrical force to the sides of the distal end of one or more of the articulable beak tips, according to embodiments. As shown, these first and second tendons 468, 470 may be configured to selectively apply a proximally-directed force and a distally-directed force to the distal portion to cause a first and second articulable beak tips 452, 454 to assume their closed and open configurations, respectively, or in the case of a single beak configuration, to open or close against a fixed or non-articulable beak (not shown in this view). Indeed, pulling on the first and second tendons 468, 470 by a proximal force acting on actuating element 469 tends to close the first and second articulable beak tips 452, 454 (i.e., draw the respective distal tips closer to the longitudinal axis and closer to one another). Pushing on the first and second tendons 468, 470 tends to open the first and second articulable beak tips 452, 454 (i.e., draw the respective distal tips away from the longitudinal axis and away from one another).

Figure 2B:
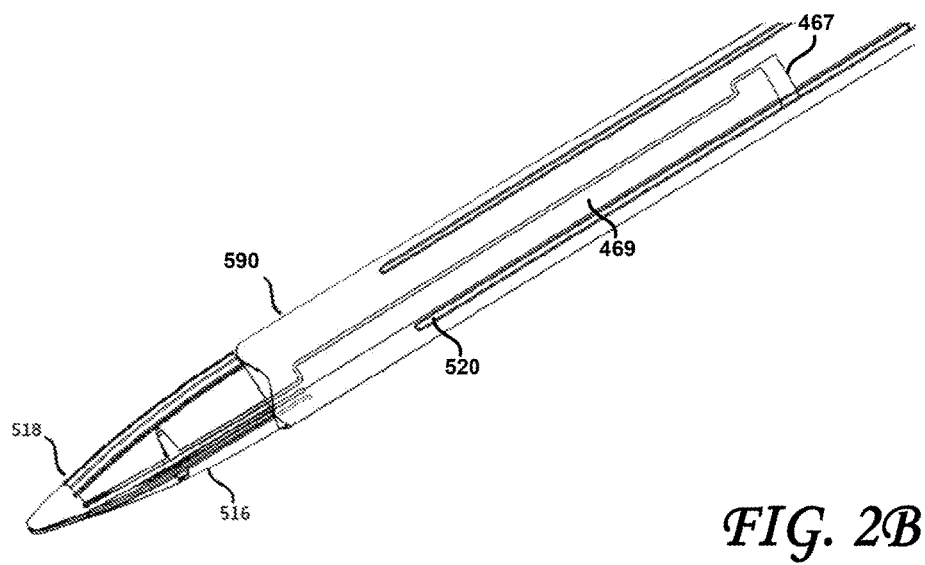

FIG. 2B shows a work element (shown as cutting elements 13 in FIG. 1 for clarity) consisting in one embodiment of twin articulable beaks 516 and 518 (numbered differently in this illustration to indicate that an entire beak or beaks may be comprised of many features already outlined in FIG. 2A) and outer or distal sheath (an outer sheath and a distal sheath may both be present in embodiments) of an excisional device according to embodiments. As shown, an excisional device, according to one embodiment, may comprise an outer or distal sheath 590 defining a longitudinal axis whose distal end, as shown, may comprise a variety of shapes, such as wavy or sinusoidal shapes or other leading edge shape, with such leading edge being sharpened around its circumference and sides as desired. A work element may be configured to at least partially fit within an outer or distal sheath 590 and be configured to be withdrawn into the distal sheath 590 and extend out of its tip while lying within its curvature. A work element, according to one embodiment, may comprise a single articulable beak with an opposing fixed beak, or of first and second (or more) articulable beaks 516 and 518 as shown in this figure, according to various embodiments, and configured to rotate within an outer or distal sheath 590 about the longitudinal axis thereof, as shown at 517. As shown in this figure, first and second articulable beaks 516, 518 may define respective first and second curved distal surfaces configured to cut tissue. The work element may be further configured to be advanced distally such that at least first and second curved distal surfaces of a beak or first and second articulable beaks are disposed outside of an outer or distal sheath. As particularly shown in FIG. 6, a portion of both first and second curved surfaces of a single beak or first and second articulable beaks 516, 518 may be configured to rotate outside of an outer or distal sheath 590, with the remaining portions thereof rotating within an outer or distal sheath 590. Indeed, in this embodiment, a substantial portion of first and second articulable beaks 516, 518 may be configured to rotate within an outer or distal sheath 590. This configuration radially supports first and second articulable beaks 516, 518, and prevents them from over-extending or otherwise undesirably deforming when cutting through tough tissue. According to one embodiment, a shearing or scissors action may be imparted, as the distal tips of first and second articulable beaks 516, 518 rotate inside the extremity of an outer or distal sheath 590 and act with their sharpened edges against the side edges of such an outer differentially- or non-rotating sheath 590. However, first and second articulable beaks 516, 518 may also be configured to extend further out of an outer or distal sheath 590, and in either a closed or open beak configuration. A closed beak configuration wherein a work element extends only to the distal opening of an outer or distal sheath 590 may be well suited to advancing through tissue to the intended lesion site, with closed first and second articulable beaks 516, 518 blocking tissue entry into a central lumen as the tip of the device advances through the tissue. Alternatively, such extension of first and second articulable beaks 516, 518 outside of an outer or distal sheath 590 may constitute a phase of a combined rotational/closing and part-off action following coring of the tissue accomplished with first and second articulable beaks 516, 518 at least partially enclosed within an outer or distal sheath 590. Finally, extension of first and second articulable beaks 516, 518 in either the closed or open configuration may be accomplished either by extension of a work element and/or retraction of a distal sheath 590 in relation to cored or to-be-cored tissue, as will be illustrated later in figures. To limit the extent of force that may be applied to first and second tendons 468, 470 and thus on first and second articulable beaks 516, 518, a work element 13 may comprise travel limiter structures 467 (only one of which is visible in FIG. 2B). Indeed, as shown in FIG. 2B and according to one embodiment, the travel in the distal and proximal directions of beak actuating elements 469 may be limited by interlocking tab and slot features of any shape that only allow a limited relative travel between the constituent elements thereof. Such limited travel is sufficient, according to one embodiment, to fully open and to fully close first and second articulable beaks 516, 518.

Slots, such as for fluid delivery or vacuum, may be provided within an outer or distal sheath, as shown at 520. Should a vacuum be drawn within the lumen of an outer sheath 590, surrounding tissue may be drawn thereto, thereby assisting in stabilizing the distal end of the excisional device during the specimen cutting procedure. Vacuum slots may also serve to collect liquids and free cells from the surrounding tissue or to deliver liquids to the surrounding tissue. They may also serve as an opening at the distal end of the device so that as vacuum is applied internally at the proximal end of a distal (e.g., outer, in this illustration) sheath 590 as an aid in transporting tissue specimens proximally, a corresponding vacuum is not built up behind (distally) the tissue specimens, which may prevent them from acting as plugs in a work element.

The shape of sharp cutting elements or beaks in assembly 13, such as the embodiment thereof shown in FIGS. 2A and 2B, for example, provides substantial support vectors for all movements required of such cutting blades during rotation, opening/closing and axial motions (not shown). Using the nomenclature of FIG. 1 in particular, this embodiment enables sharp cutting elements of beak assembly 13 to be made extremely thin, which fulfills a requirement that for any given outer radial dimension of a tubular coring and transport assembly 11, including a cutting beak assembly (see also FIG. 1), the caliber of the core sample retrieved from the patient will be as large as possible. The shape(s) of sharp cutting elements of beak assembly 13 specified for use in coring and part-off, according to embodiments, enable the biopsy device 10 to obtain a full diameter core sample, and in fact larger than full diameter due to dimensions of a coring and transport assembly 1, of which slightly larger caliber (e.g., diameter) may be desirable in order to compress, "stuff", or pack in as much tissue sample as possible into a tubular coring and transport assembly 11. Coring of a larger than full diameter tissue sample may prove advantageous from diagnostic and clinical standpoints, by providing more sample (not shown) for analysis or by removing as much of the target tissue as possible during a single excision.

According to one embodiment and as described herein, the work element 13 of FIG. 1, including articulable beak(s) 516 and 518 of FIG. 2B, may be configured for rotation within an outer non- or differentially-rotating outer or distal sheath(s), such as 590 of FIG. 2B. Moreover, articulable beak(s), according to one embodiment, may comprise a surface having substantially the same curvature as the body portion. According to one embodiment, articulable beak(s) may be generally described as being or comprising one or more hyperbolic segments of one or more sections of a hollow cylinder, such as a hypo tube. Variations including complex curves may be incorporated into the shape of articulable beak(s), to optimize function in different sections of the edges of articulable beaks. Moreover, first and second articulable beaks, according to embodiments, may have slightly different shapes from one another. The angle formed by the distal portion of first and second articulable beaks may be, for example, from about 5 to 50 degrees. According to one embodiment, the angle may be between about 10 and 30 degrees. According to another embodiment, the angle formed by the distal portion of first and second articulable beaks may be about 18 degrees.

Note that, according to one embodiment, an entire work element, including first, or first and second (or multiple) articulable beaks 516 and 518, along with their first and second tendons, beak actuation mechanism 469, living hinges 458 (as shown in FIG. 2A) connecting first and second articulable beaks to a body portion of a work element, travel limiter structures and, as described below, a first helical element may together be a single monolithic structure formed of a same material that may be (e.g., laser-)

cut from, for example, a single solid hypo tube. That is, these structures may be formed together of a same piece of unbroken homogeneous material.

Figures 3A, 3B:
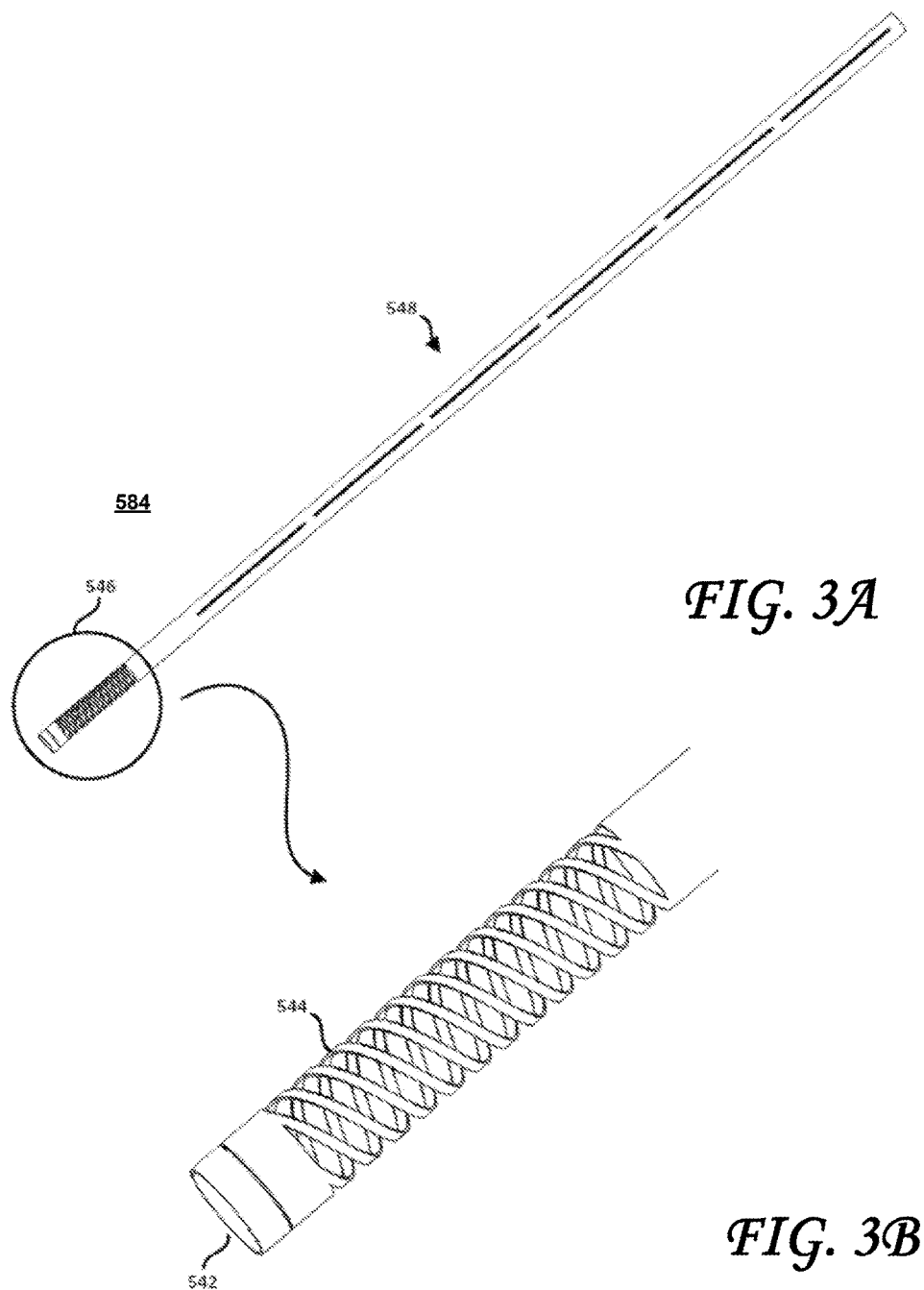
FIGS. 3A and 3B show an excisional device, according to one embodiment, with the non- or differentially-rotating outer or distal sheath removed.
Figure 5:
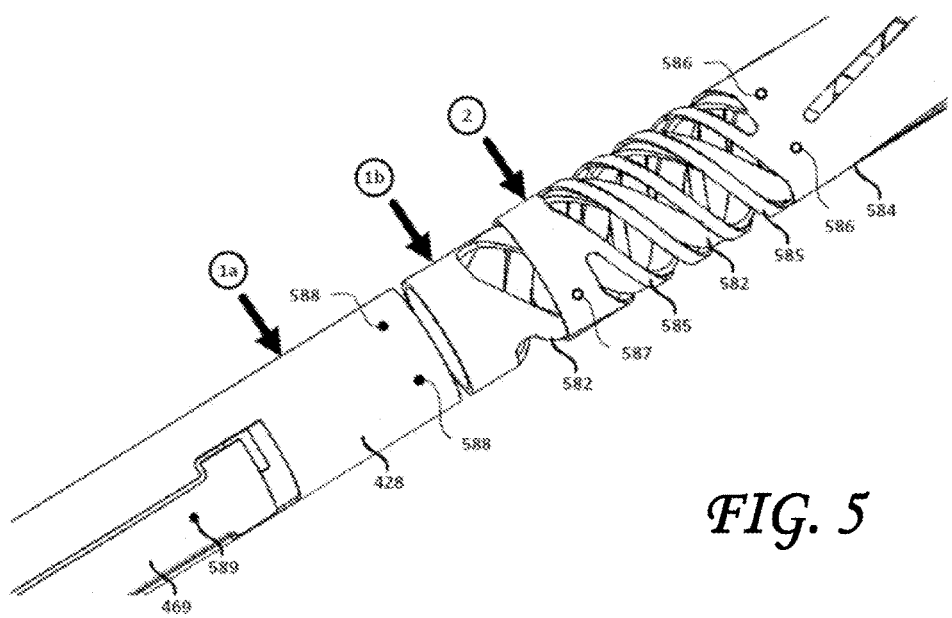
FIG. 5 shows details of a proximal sheath, beak actuation elements and inner helical element, according to embodiments.
Figure 6:
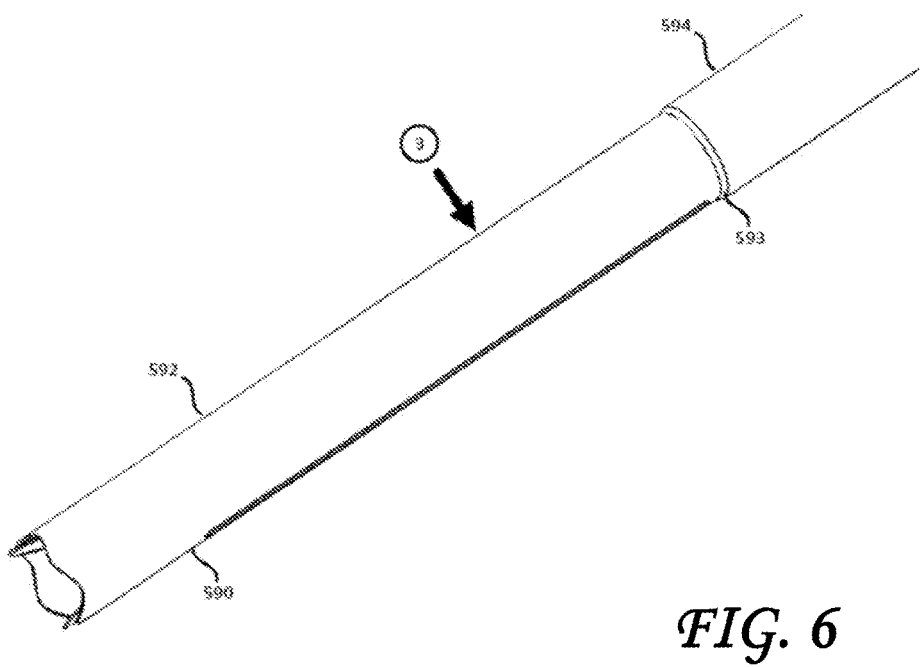
FIG. 6 shows a non- or differentially-rotating outer or distal sheath, according to embodiments.
Figure 7:
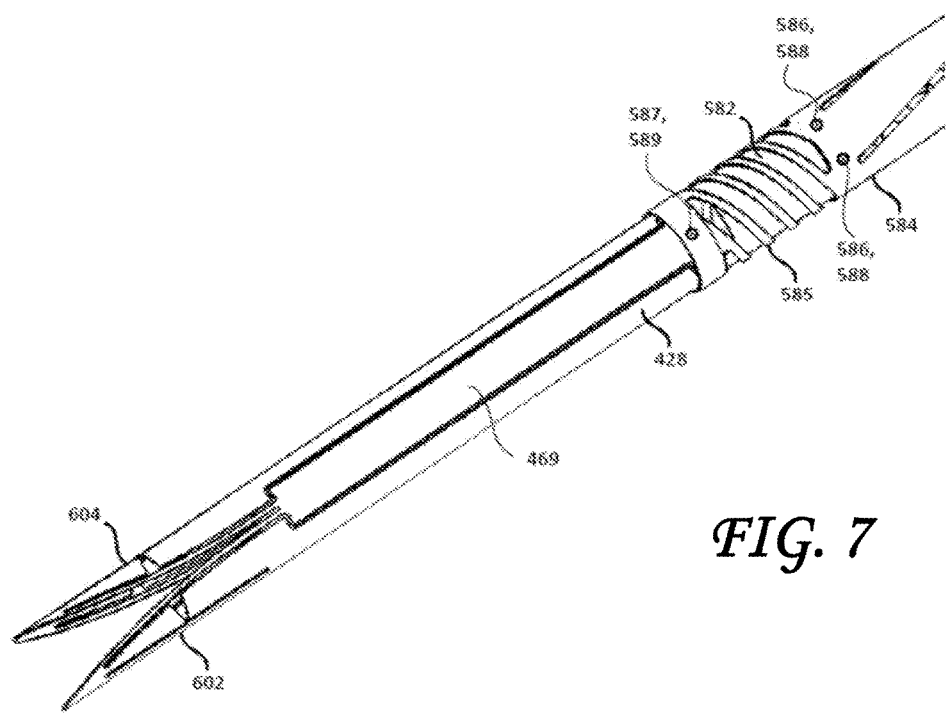
FIG. 7 is a view of a twin beak work assembly with an outer or distal sheath removed, according to embodiments.

Continuing to describe additional elements of a tubular transport and coring mechanism 11 of FIG. 1, according to embodiments, FIGS. 3A and 3B show an intermediate, proximal sheath 584 of an excisional device 10, according to one embodiment, with a non- or differentially-rotating outer or distal sheath 590 removed. According to one embodiment, a proximal sheath 584 may be configured to fit over at least a portion of a work element (as shown later in FIG. 7) and abut collar 542, which collar may be nothing more than an internal shoulder within a distal (or outer) sheath 590, such as 593 in FIG. 6 below. According to one embodiment, a proximal sheath 584 may be configured to resiliently bias a first and second articulable beaks 516 and 518, if double (or multiple) beaks are used, in the open position. According to one embodiment, a proximal sheath 584 may be slid over a work element proximal portion and advanced over a work element until the distal end thereof abuts against a collar 542 (or shoulder 593 of FIG. 6). Therefore, as will be shown later in FIG. 7 and other figures, selectively acting upon (e. g., exerting a proximally-directed or distally-directed force) a proximal sheath 584 by action on its proximal portion 548 causes a first and second articulable beaks 516, 518 to open and close, in concert with a distal sheath 590 of FIG. 6 over at least a portion of a work element. In such an embodiment, a proximal sheath 584 may itself be enclosed by an outer non- or differentially-rotating distal sheath 590, effectively capturing the distal portion 546 of a proximal sheath against a distal sheath 590, as shown in FIGS. 6 and 7 further on. According to one embodiment, a proximal sheath 584 may be either free floating or driven in rotation. According to another embodiment further detailed below, a collar 542, which is primarily shown for illustrative purposes of one embodiment, may be eliminated and a beak actuating element (469 of FIGS. 1A and 2B above) of a work element may be directly attached to the distal end of proximal sheath 584 at the distal and proximal ends of a helical portion 544 of a proximal sheath. In such an embodiment, a work element may be attached to a proximal end of a helical element 544 to rotate a work element (including a first and second articulable beaks). In this manner, a proximal sheath 584 may be configured to entrain a work element in rotation as well as to open and close articulable beaks. In such an embodiment, an inner or first helical element, such as will be shown in FIG. 5, may be decoupled from a work element, thereby enabling such inner or first helical element to be driven at a rotational speed that is independent of the rotation speed of a connected proximal sheath and first or first and second articulable beaks 518 or 516, 518, as is shown and discussed in greater detail below. According to one embodiment, to bias a first and second articulable beaks 516, 518 in the open position (at least partially within an outer or distal sheath 590, according to one embodiment), a proximal sheath 584 may comprise a second helical element 544. In this manner, according to one embodiment, not only may the present excisional device comprise first or first and second helical elements, but such helical elements may be co-axially arranged within the device, one over the other. According to one embodiment, at least a portion of a second helical element may fit over a first helical element within the excisional device, to effectively define a structure comprising a coil-within-a-coil.

It is to be noted that, herein, the phrase "helical element" and the terms "helix" or "helices" are intended to encompass a broad spectrum of structures. Indeed, the structures shown herein are but possible implementations of a helical element, helix or helices. According to other embodiments, "helical element", "helix" or "helices" and equivalent expressions may be implemented as tubes having one or more slot-shaped openings or fenestrations along at least a portion of the length thereof. Such fenestrations may be substantially parallel to the longitudinal axis of a tube or may be disposed, for example, in a spiral configuration. The fenestrations may be continuous along at least a portion of the length of a tube or may be discontinuous, such as to result in a plurality of such parallel or spirally wound fenestrations. The fenestrations may be very wide such that the resultant structure resembles a spring, or more narrow, such that the resulting structure more closely resembles a tube having narrow, slot-shaped openings therein. The continuous or discontinuous fenestrations may be caused to assume other configurations along at least a portion of the tubes in which they are formed. For example, the fenestrations may be caused to form a zigzag pattern such as "NNNN . . . ", "/VVVVV" or "VVVV . . . " or a cross-shaped pattern, such as "XXXXX". Significantly, the terms "helical element," "helix," or "helices" should be understood to cover a spectrum of structures, from a spring-like structure to tubes having selected slot-shaped openings.

According to one embodiment, a proximal sheath 584 may comprise a distal region 546 comprising a second helical element 544 and a proximal region 548. A region 548 may be generally co-extensive with at least a portion of a first helical element, if included in such embodiment, of a work element and may comprise structure configured to aid in the proximal transport of a severed tissue specimen. Indeed, after being severed from surrounding tissue, the cored specimen may be urged in the proximal direction within the body portion of the work element and eventually engage such a rotating first helical element, if present, along with a flush conduit to aid tissue transport. A first helical element, if present according to embodiments, may assist in the transport of the cored specimen to a tissue collection magazine 27 of FIG. 1 coupled to the present excisional device 10. Surface features may be provided on the surface of an inner lumen of a proximal sheath 584. Such features, however configured, may aid in the transport of cored specimen by providing some measure of friction between the cored specimen and a rotating first helical element, if used, to enable the cored specimen to move in a proximal direction through the device. According to one embodiment and as shown in FIGS. 5 and 7 further on, when a proximal sheath 584 is fitted over a work element, tissue entrained by a first helical element, illustrated by 582 of FIGS. 5 and 8, will also be drawn against an inner lumen of a proximal sheath 584. According to embodiments, a flush and a vacuum may be drawn within at least a proximal sheath 584. In this manner, cored tissue specimen(s) may be drawn through coils of a first helical element, if present, to come into intimate contact with the (e.g., patterned or slotted) surface of a proximal sheath's inner lumen, and tissue specimen transport may be aided by flush and/or vacuum drawn within such proximal sheath's inner lumen. In other embodiments, only the flush fluid and vacuum, acting in concert but without a first helical element, may suffice to ensure tissue specimen transport to, for example, a transfer magazine.

Figure 4:
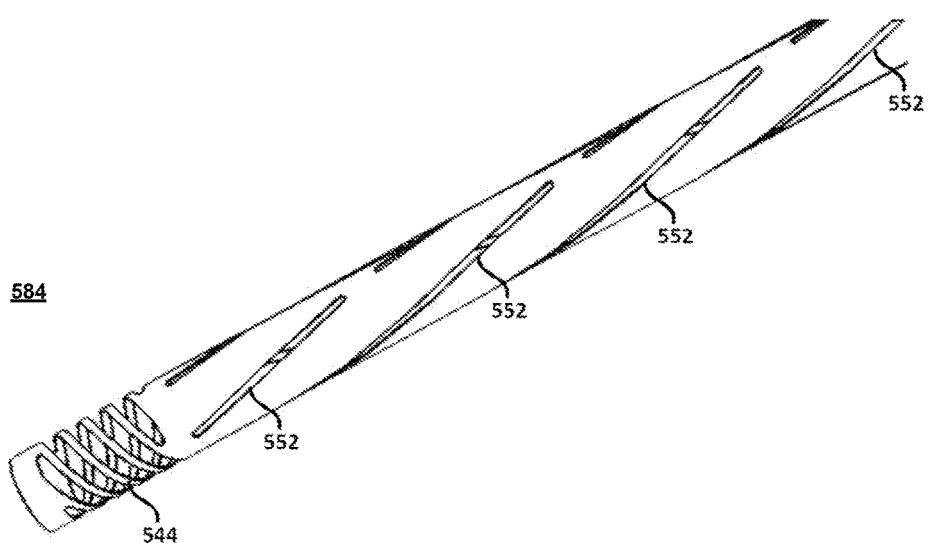
FIG. 4 shows a proximal sheath comprising a plurality of elongated slots disposed in a spiral pattern around a longitudinal axis, according to one embodiment.

FIG. 4 shows a proximal sheath 584 comprising a plurality of elongated slots disposed in a spiral pattern around a longitudinal axis, according to one embodiment. As shown in FIGS. 3A and 3B, and according to one embodiment, a proximal sheath 584 may define one or more elongated slots 552 therein. Such slots 552 may allow fluid communication with an interior lumen of a proximal sheath 584. In other words, the slot or slots 552 may go all of the way through the wall thickness of a proximal sheath 584. For example, when vacuum is drawn within a central lumen of a proximal sheath, cored tissue specimens being transported by a first rotating helical element 582, if used, may be drawn to slots 552, and partially invaginated therein, to provide some resistance to the cored tissue specimen, thereby preventing the specimen(s) from simply rotating in place within a first helical element without moving. Slots 552 may also serve as controllable conduits for flushing liquids used to aid transport in concert with aspiration applied from a vacuum source within or external to the device 10. According to one embodiment, slots 552 may be serially disposed end-to-end substantially parallel to the longitudinal axis of a proximal sheath 584, as shown in FIG. 3A, or may be offset relative to one another, or may be disposed in a spiral pattern (whether non-overlapping or overlapping, as shown in FIG. 4), thus effectively acting as an elongated co-axially disposed third helical element of similar or different pitch than a second helical element, similar to that discussed under FIG. 3B above.

FIG. 5 shows details of a proximal sheath, beak actuation elements and an inner first helical element, according to embodiments. It is to be noted that the figures herein are not to scale and the relative dimensions of any constituent elements of the excisional device 10 may vary from figure to figure. According to one embodiment, the working end (e.g., substantially all structures distal to the handle portion 12) of the excisional device 10 may be essentially composed or formed of two or more separate elements that are disposed substantially concentrically or co-axially relative to one another. This results in a mechanically robust working end of the excisional device that is economical to manufacture and to assemble.

As shown in the exploded view of FIG. 5, one embodiment describes a work element that comprises body portion 428 and tendon actuating elements 469 (only one of which is shown in this view), and may be terminated by first and second articulable beaks (not shown in this view). A first helical (tissue transport) element 582 may be formed of the same material as a work element. According to one embodiment, a work element (i.e., body portion 428, tendon actuation element 469 and first or first and second articulable beaks) and a first helical element may be cut or formed from a single piece of material, such as a hypo tube. For example, hypo tube may be suitably (e.g., laser) cut to form body portion 428, tendon actuation elements 469, first and second articulable beaks and a first helical element 582. A first helical element 582 may then be mechanically decoupled from a work element by cutting the two structures apart. These two structures are, therefore, labeled (1a) and (1b) in FIG. 5, to suggest that they may have been originally formed of a single piece of material. That a first helical element is mechanically decoupled from a work element enables the rotation of a first helical element 582 to be independent of the rotation of a work element. For example, a first helical element 582 may rotate at a comparatively slower rate than the rate of rotation of a work element, as transport of severed tissue specimen may not require the same rate of rotation as may be advisable for a work element. According to one embodiment, a first helical element 582 may rotate slower than a work element of the excisional device.

The second of the three separate elements of the working end of the excisional device, in this embodiment, is a proximal sheath 584, as shown at (2) in FIG. 5. A proximal sheath 584 may comprise, near its distal end, a second helical element 585. As shown in FIG. 5, a second helical element 585 may be disposed concentrically over a portion of a first helical element 582. According to one embodiment, a proximal sheath 584 may comprise one or more proximal locations 586 and one or more distal locations 587. Proximal and distal locations 586, 587 may define, for example, indentations or through holes and may indicate the position of, for example, spot welds (or other attachment modalities) that may be configured to mechanically couple a proximal sheath 584 with a work element 1a (or 13, as shown in previous figures) of the excisional device. When assembled, a proximal sheath 584 may be concentrically disposed over a first helical element 582 and advanced such that one or more proximal locations 586 on a proximal sheath 584 are aligned with corresponding one or more proximal attachment locations 588 on a work element, and such that one or more distal location or locations 587 on a proximal sheath 584 is or are aligned with corresponding one or more distal attachment location(s) 589 on a tendon actuating element 469. The corresponding locations 586, 588 and 587, 589 may then be attached to one another. For example, one or more proximal locations 586 on a proximal sheath 584 may be spot welded to corresponding one or more proximal attachment locations 588 on a work element, and one or more distal locations 587 on a proximal sheath 584 may be spot welded to corresponding one or more distal attachment locations 589 on tendon actuating elements 469.

It is to be noted that locations 586, 587, 588 and 589 shown in the figures are illustrative and exemplary only, as there are many ways of mechanically coupling or attaching a proximal sheath 584 to a work element, as those of skill may recognize. According to one embodiment, a proximal sheath 584 may be attached such that movement of a second helical element 585 (e.g., extension and compression) correspondingly actuates first and second articulable beaks between a first (e.g., open) configuration and a second (e.g., closed) configuration. Indeed, a proximal sheath 584 may be mechanically coupled to a work element of the excisional device such that, for example, a proximal portion thereof (e.g., at or in the vicinity of proximal locations 586) is attached to the body portion 428 of a work element and such that a distal portion thereof (e.g., at or in the vicinity of distal location 587) may be attached to tendon actuating elements 469. In this manner, compression and extension of a second helical element 585 may cause a relative displacement of tendon actuation elements 469 and a body portion 428 (i.e., one may move while the other is immobile or substantially so, or both may move relative to one another), thereby causing the actuation of first and second articulable beaks.

FIG. 6 shows a non- or differentially-rotating distal sheath 590, which may or may not, according to embodiments, extend over first or first and second articulable beaks. A third of three coring and transport mechanism 11 elements, according to embodiments, is a distal sheath 590 which may be configured to fit over a work element as shown in FIG. 5 comprising a body portion 428, a tendon actuating element 469 and at least a portion of a first or first and second articulable beaks. An outer or distal sheath 590 may also be configured to slide and fit over a proximal sheath 584 that is mechanically coupled to a work element, and may have slots, similar to 552 of a proximal sheath 584 of FIG. 4 (which may essentially define a fourth helical element). An outer or distal sheath 590, according to one embodiment, may comprise a distal portion 592 (shown extended to the tips of the beaks within, but which may be shortened all the way to just distal of shoulder 593) having a first diameter and a proximal portion 594 having a second diameter. A second diameter may be larger than a first diameter. To accommodate the differences in diameters of first and second portions 592, 594, a distal sheath may comprise a shoulder 593 with a surface that transitions between distal and proximal portions 592, 594 of differing diameters and against which the distal portion of a second helical element 585 of FIG. 5 may act, in one embodiment.

FIG. 7 is a view of a two beak assembly with a distal sheath 590 removed, according to embodiments. FIG. 7 shows components of a work element (comprising, e.g., body portion 428, one of a tendon actuation elements 469 and first and second articulable beaks 602, 604) mechanically coupled to a proximal sheath 584. As suggested at 586, 588 and at 587, 589, a proximal sheath 584 may be spot welded to a work element in such a manner as to enable differential motion of a body portion 428 of a work element relative to the tendon actuating elements 469 thereof when a second helical element 585 compresses and extends, which differential motion actuates (e.g., opens and closes) first and second articulable beaks 602, 604. Significantly, the attachment of a proximal sheath 584 to both a body portion 428 and to tendon actuating elements 469 of a work element results in substantially equal torque being imposed on the constituent elements of a work element, thereby maintaining the structural integrity of a work element as it is spun up to speed (by rotating a proximal sheath 584 in this embodiment) and as first and second articulable beaks 602, 604 cut through variably dense, fibrous and vascularized tissues.

Figure 8:
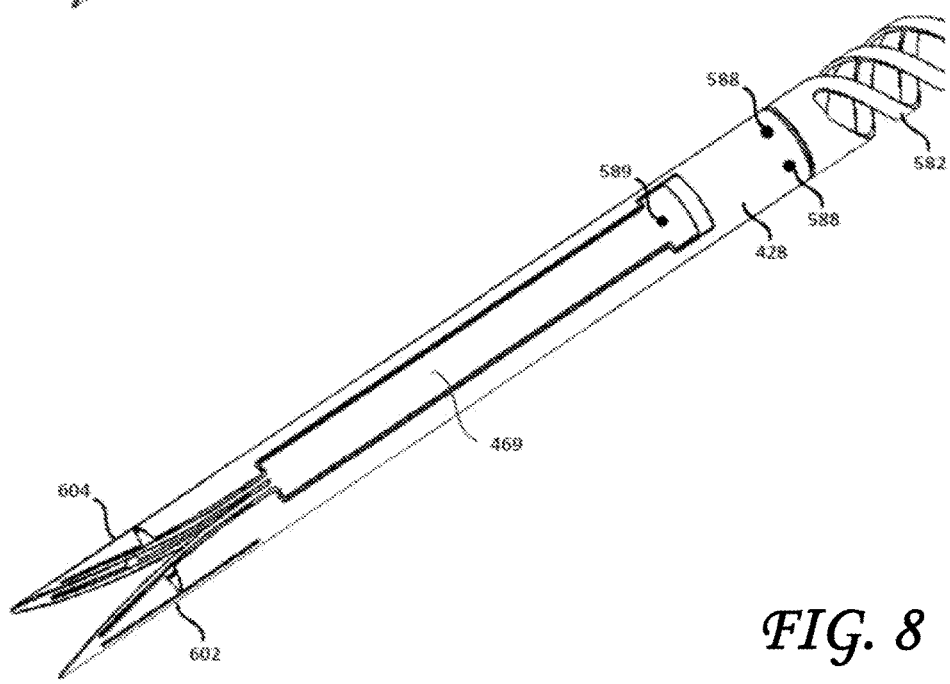
FIG. 8 is a view of a twin beak work assembly with an outer or distal sheath and proximal sheath removed, according to embodiments.

FIG. 8 is a view of a multiple beak 602, 604 assembly with an outer or distal sheath and proximal sheath removed, according to embodiments. FIG. 8 shows a body portion 428, tendon actuation element 469 and first and second articulable beaks 602, 604 of a work element 13 together with a first helical element 582. A proximal sheath 584 and a distal sheath 590 are not visible in this view. As shown, a first helical element may be co-axially disposed relative to a body portion 428 of a work element and may be of the same or substantially the same diameter. As noted above, the two may be formed of or cut from a single piece of material such as, for example, a stainless steel hypo tube. According to another embodiment, a first helical member may be of a different diameter than a body portion 428. However, such an embodiment may require corresponding changes to the diameters of a proximal sheath 584 and a proximal portion 594 of a distal sheath 590 and a change to the shoulder 593, as previously illustrated herein. Thus far and according to the previous figures as discussed above, embodiments of a tubular coring and transport assembly (FIG. 1) of the device may comprise first (transport or inner helix), second (beak actuation helix of the proximal sheath) third (proximal sheath slots) and even fourth (distal sheath slots) helices co-axially disposed to each other. Embodiments discussed in later figures will show other configurations wherein there may be less than three co-axially disposed helical elements in device 10.

FIGS. 9A and 9B show another embodiment of a work element, according to one embodiment. Attention is drawn to the proximal end of a work element 13. Therein, a body portion 428 of a work element 13 may be mechanically coupled to tendon actuating element 469 at the proximal end of a work element. Note that a tendon actuating element 469, from the embodiment of FIGS. 2A and 2B, is already coupled to a body portion 428 through tendons 468, 470, toward the distal end of a work element 13. That is, an entire work element 13 may be formed of a single homogeneous material—such as from a single hollow tube that is (for example) laser-cut to form the structures shown in FIGS. 9A and 9B. Two beaks are shown. It is to be understood, however, that such need not be the case, as a work element 13 may comprise multiple beaks or a single beak that acts against a non-moveable part, such as a fixed trough-shaped distal portion of a distal sheath or against a fixed, opposing beak that is part of a work element 13 itself.

According to one embodiment, as shown in FIGS. 9A and 9B, the proximal end of a tendon actuating element 469 may be mechanically coupled to the proximal portion of a body portion 428. Such mechanical coupling may be configured to maintain a tendon actuating element centered on the cutout in a body portion formed to accommodate a tendon actuating element 469 and/or to provide additional biasing force in the distal direction, as well as to aid in manufacturing. One embodiment comprises a resilient member 427 having one end thereof coupled to a tendon actuating element 469 and another end thereof coupled to a proximal portion of the work element 13. Such a resilient member 427 may be configured to bias the beak or beaks of a work element 13 in the open configuration, such that a sufficiently great proximally-directed force applied to a tendon actuating element 469 tends to close a beak or beaks. Conversely, release of such proximally-directed force causes a resilient member 427 to release the energy stored during the extension thereof and return to its un-extended state, thereby exerting a distally-directed force on a tendon actuating member 469, which causes a beak or beaks to return to its or their default open configuration.

Also shown in FIG. 9B, attachment holes 292A and 292B (similar in function to 588 and 589 of FIG. 5 above) may be provided on a body portion 428 and on a tendon actuating element 469, respectively. Such attachment holes 292 may, according to one embodiment, indicate the location of, for example, spot welds, as detailed below.

Figure 9:
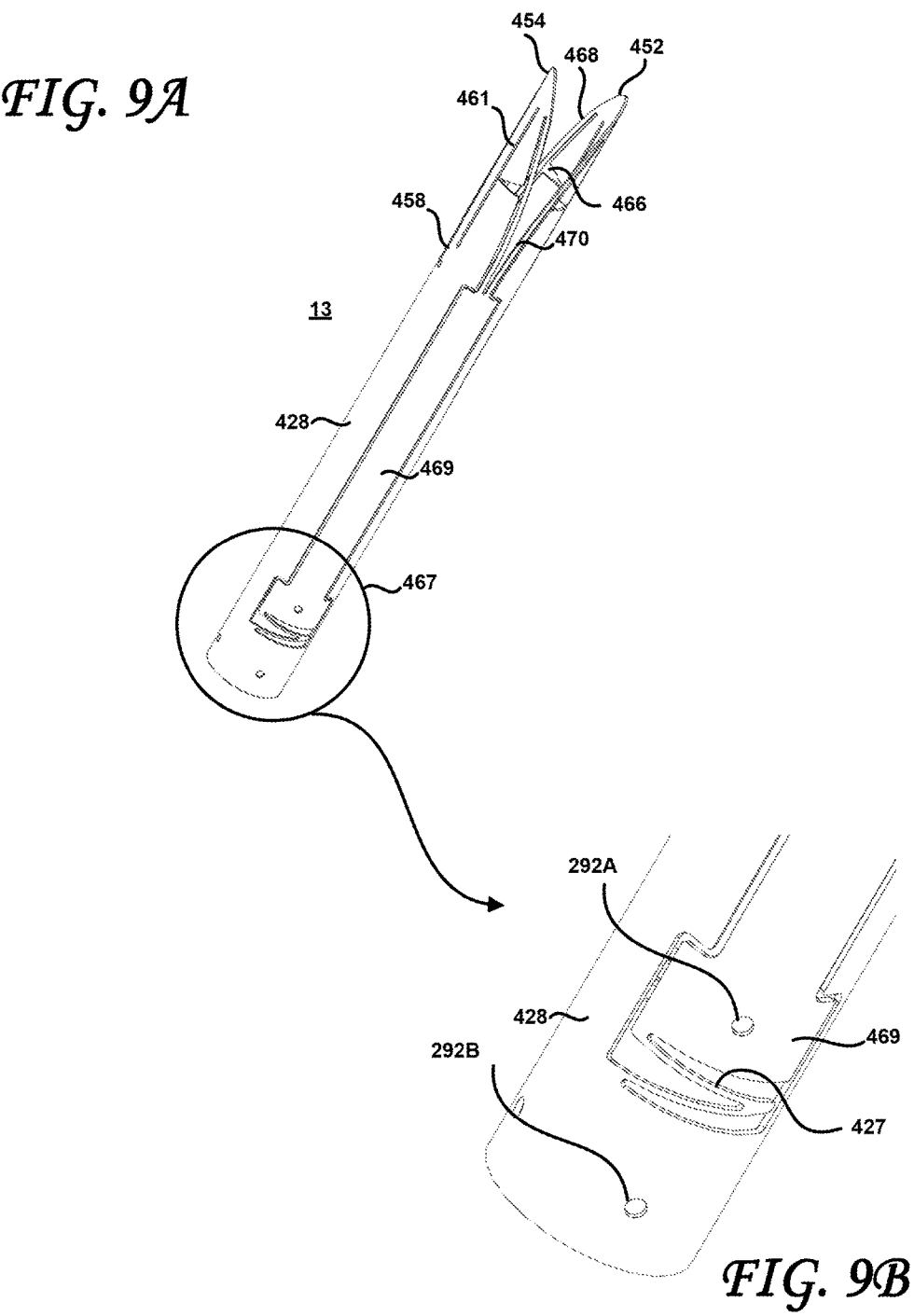
FIG. 9A shows a monolithic beak assembly of an excisional device according to one embodiment.
FIG. 9B shows a detail of a proximal end of a monolithic beak assembly of an excisional device according to one embodiment.
Figure 10:
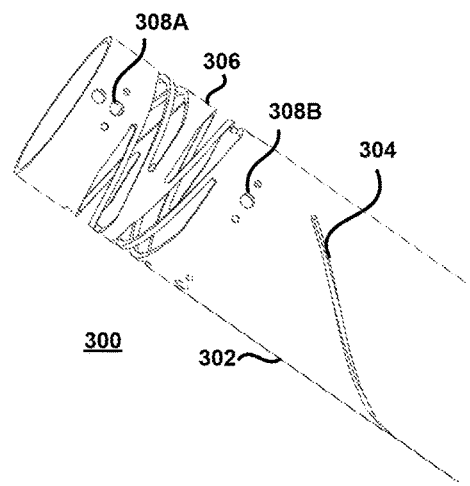
FIG. 10 shows the distal end of a proximal sheath of an excisional device according to one embodiment.
Figure 11:
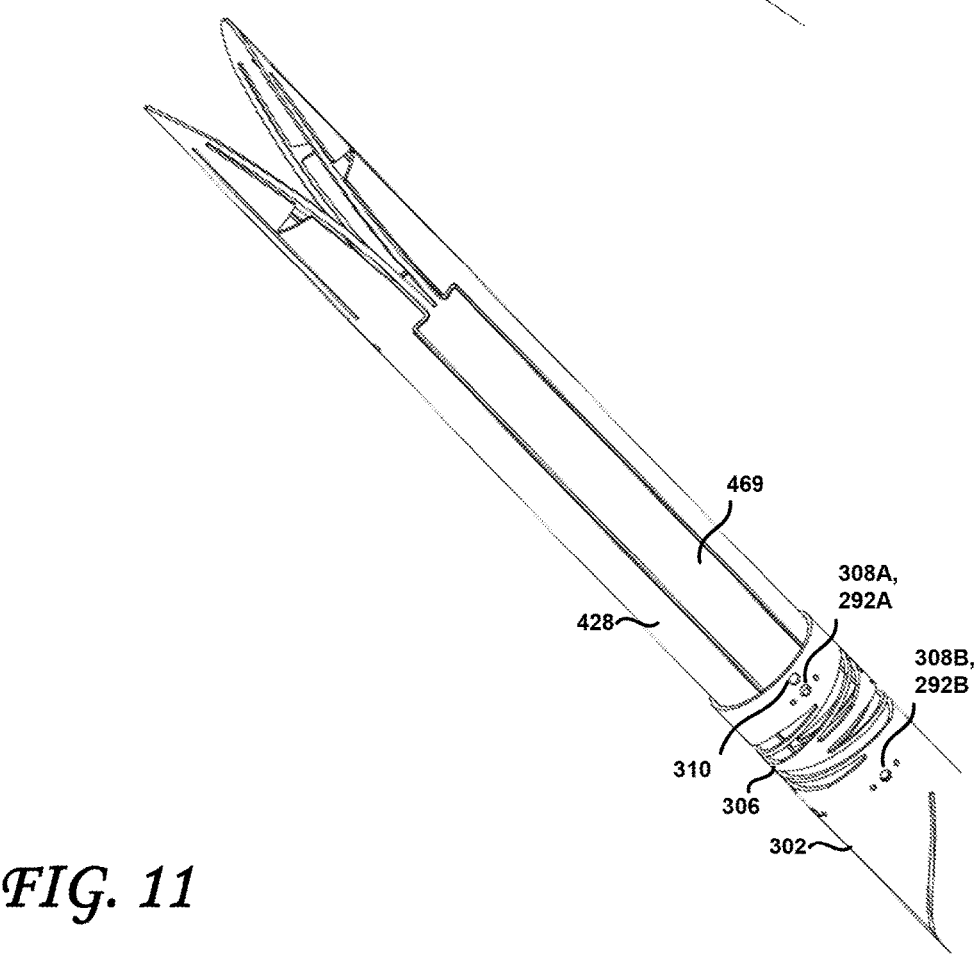
FIG. 11 shows an assembly comprising a monolithic beak assembly and a proximal sheath of an excisional device according to one embodiment.

FIG. 10 shows a distal portion of a proximal sheath according to one embodiment. A proximal sheath 300, as shown in FIG. 10 may comprise a number of fenestrations or slots 304 that run through the wall of a proximal sheath 300, from an outer surface to an interior lumen thereof. The distal portion of a proximal sheath 300 may be configured to fit over and attach to the proximal end of a monolithic beak assembly 13 of FIGS. 9A and 9B. During assembly of the present excisional device and as shown in FIG. 11, attachment holes 308A and 308B of a proximal sheath 300 may be lined up with attachment holes 292A and 292B, respectively, of a monolithic beak assembly 13. A proximal sheath 300 may thus be attached to a monolithic beak assembly 13 at attachment points 292A, 308A and 292B, 308B. According to one implementation, an attachment point 308A of a proximal sheath 300 may be spot-welded to an attachment point 292A of a tendon actuating member 469 of a monolithic beak assembly 13. Although not shown in these figures, corresponding attachment points may be provided on the hidden side of the device. Similarly, an attachment point 308B of a proximal sheath 300 may be spot-welded to an attachment point 292B of a body portion 428 of a monolithic beak assembly 13. As also shown in FIG. 10, the distal portion of a proximal sheath 300 may define a resilient or spring portion, as shown at reference numeral 306.

Figure 12:
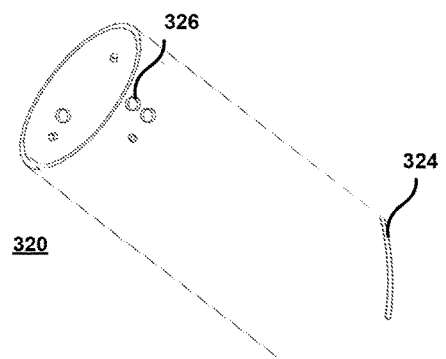
FIG. 12 shows the distal end of a distal sheath of an excisional device, according to one embodiment.
Figure 13:
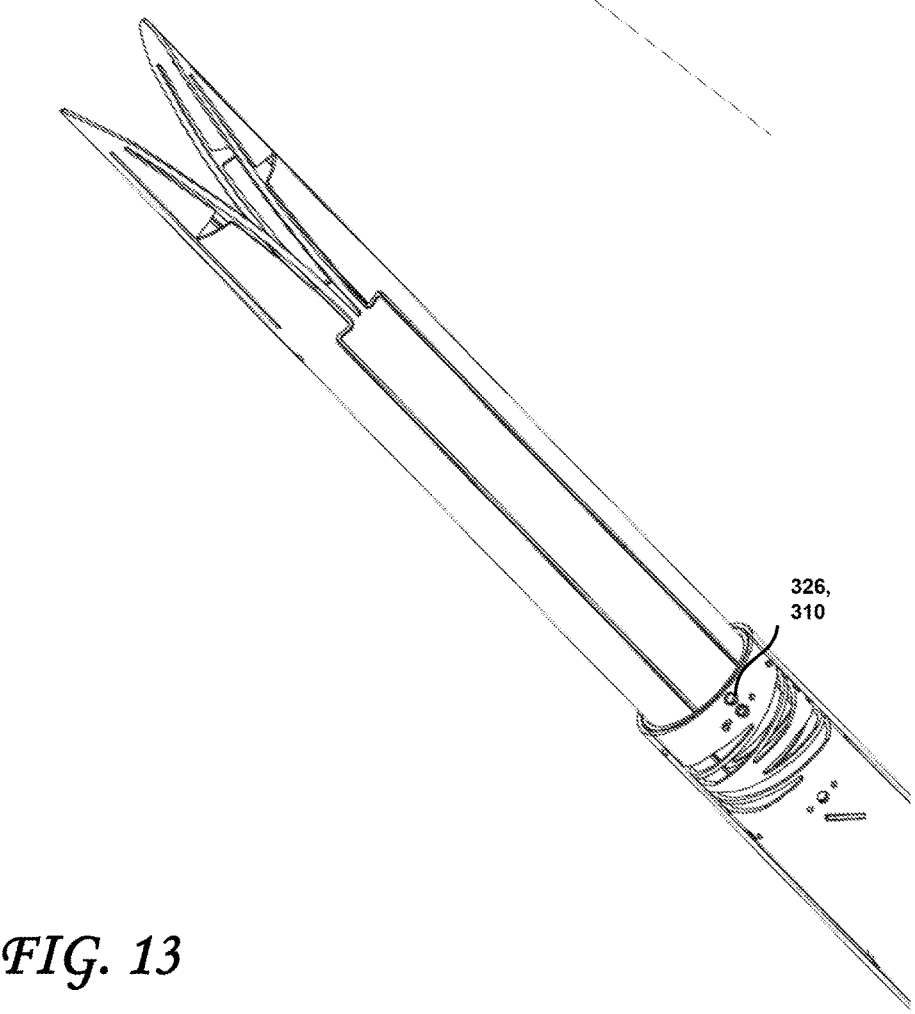
FIG. 13 shows an assembly comprising a monolithic beak assembly, a proximal sheath and a distal sheath, according to one embodiment.

FIG. 12 shows the distal portion of a distal sheath 320 (noted as 590 in previous figures), according to one embodiment. A distal sheath 320 may be configured to fit over a proximal sheath 300 and an attachment point 326 of a distal sheath 320 attached to attachment point 310 on a proximal sheath 300, as shown in FIGS. 11 and 13. For example, an attachment point 326 of a distal sheath 320 may be spot-welded to attachment point 310 on a proximal sheath 300, as suggested in FIG. 13. A distal sheath 320 is transparently illustrated in FIG. 13, to show underlying detail. It is to be understood that spot-welding is but one method of attaching constituent components of the present excisional device to one another. Other attachment technologies may also be used, as appropriate. Once a distal sheath 320 is spot welded in place, it will rotate in synchronicity with a beak assembly 13 and proximal sheath 300, but will be able to move axially relative to proximal sheath 300. Such axial movement between distal and proximal sheaths will positively open and/or close a beak or beaks of monolithic beak assembly 13, as previously discussed.

Figure 14:
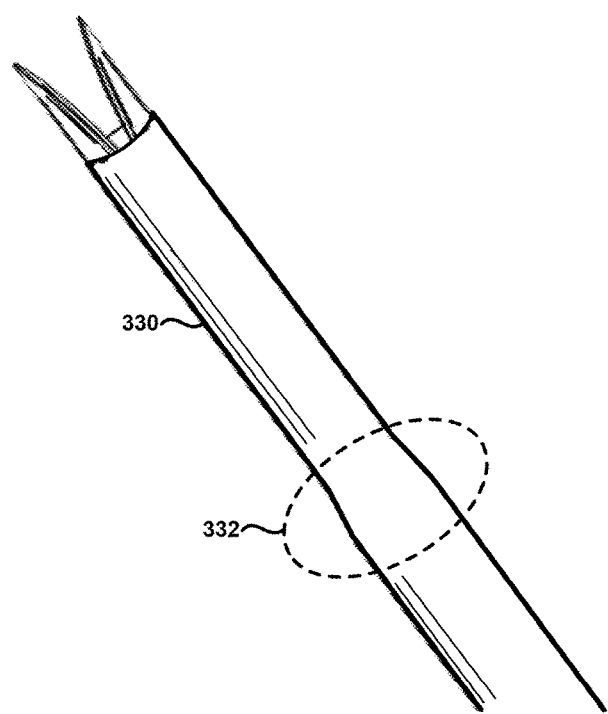
FIG. 14 shows the distal portion of an excisional device according to one embodiment.

FIG. 14 shows one embodiment of the present excisional device, in a still further intermediate state of assembly. In FIG. 14, an outer sheath 330 (also shown as 590 in previous figures, but now re-numbered to distinguish over a distal sheath 320) has been fitted over an assembly comprising a monolithic beak assembly 13, a proximal sheath 300 and a distal sheath 320. For example, an outer sheath 330 may comprise polyimide or may comprise or be formed of stainless steel among other suitable materials. An outer sheath 330 may be configured to be manually rotating, non-rotating, or at least differentially-rotating with respect to an assembly comprising a monolithic beak assembly 13, a proximal sheath 300 and a distal sheath 320 and may further be configured to be removable. That is, in this embodiment, while an assembly comprising a monolithic beak assembly 13, a proximal sheath 300 and a distal sheath 320 may rotate at relatively high rates of speed (in the thousands of revolutions per minute, for example), an outer sheath 330 may be held either stationary or rotated as needed. This may be accomplished manually or otherwise actuated by any mechanical means. For example, the user may rotate an outer sheath 330 a few tens of degrees at a time, as and when the procedure requires, and may remove or replace it before, during or after a procedure. An outer sheath 330 may extend distally to beaks of a monolithic beak assembly 13 (similar to that shown in FIG. 6), may expose a greater proportion of a monolithic beak assembly 13 or may cover a significant portion of beaks, which may be controlled during use, according to embodiments.

According to one embodiment, an outer sheath 330 may be dimensioned so as to allow an annular space to exist between the inner wall of an outer sheath 330 and the combined outer surfaces of a distal sheath 320 and distal portion of a monolithic beak assembly 13. This annular space may allow for flush to be introduced at selected stages in the procedure. The flush may provide lubrication for the rotation of an assembly comprising an assembled monolithic beak assembly 13, a proximal sheath 300 and a distal sheath 320, and may facilitate the rotation and thus the transport of the cored and severed tissue specimen in the distal direction. According to one embodiment, when the beak or beaks of a monolithic beak assembly is or are in the open configuration, fenestrations or slots 304 (FIG. 10) defined in a proximal sheath 300 are not lined up with fenestrations or slots 324 (FIG. 12) defined in a distal sheath 320. However, according to one embodiment, when beak or beaks are actuated, and beaks are closing, are closed or are substantially closed, then fenestrations or slots 324 defined in a distal sheath 320 become lined up (or substantially lined up) with corresponding fenestrations or slots 304 defined in a proximal sheath 300. In this state, if there is flush in an annular space between the outer surface of a distal sheath 320 and the inner wall of an outer sheath 330, this flush will enter the interior lumen of the device (where the cored and severed tissue specimens are collected and are transported). Moreover, as the flush may have been entrained into rotation in an aforementioned annular space as the assembly comprising a monolithic beak assembly 13, a proximal sheath 300 and a distal sheath 320 rotates, the rotating flush may enter this interior lumen with some force and may exert that force on any cored and severed tissue specimen therein. This flush may act as a lubricant as well to the specimen contained in the inner lumen of the device. According to one embodiment, a vacuum may be drawn within the interior lumen of the device. According to one embodiment, the vacuum force imparted on the cored and severed tissue specimen, alone or together with force imparted on such specimen by flush entering this interior lumen, draws and transports the cored and severed tissue specimen in the proximal direction, for eventual transport to a transfer magazine 27, for example.

Transport of cored tissue specimens may be aided by a shoulder shown at 332 in FIG. 14. Indeed, such shoulder encompasses the location defined by the proximal end of a monolithic beak assembly 13 and the distal end of a proximal sheath 300 as well as the distal end of a distal sheath 520. As the diameter of a proximal sheath 300 is somewhat greater than that of the proximal end of a monolithic beak assembly 13, the interior lumen of a proximal sheath 300 is correspondingly larger than the interior lumen of a monolithic beak assembly 13, and the interior lumen of a proximal sheath thus serves as an expansion chamber. As the cored and severed tissue specimen(s) enters the interior lumen of a monolithic beak assembly 13, the tissue specimen(s) may be somewhat compressed. Such compression may be somewhat relieved as the tissue specimen(s) transitions from the lumen of a monolithic beak assembly 13 to the somewhat greater diameter lumen of a proximal sheath 300, at shoulder 332. This decompression of the tissue specimen(s) in the lumen of a proximal sheath 300 may, together with flush and/or vacuum, also facilitate tissue transport. A shoulder at 332 could expand an inner lumen diameter in the range of 0.001 inch to 0.100 inch additional over an original lumen diameter, or double a lumen diameter, whichever is greater. As previously mentioned, shoulder features may be incorporated into a proximal sheath, distal sheath and outer sheath to augment such tissue expansion/transport action. As previously mentioned may be the case, such an embodiment may not incorporate a first helical element (transport helix) similar to that shown in FIG. 5 above, but may instead be constituted of co-axially disposed helices, in the form of a proximal sheath and a distal sheath, which, aided by flush and/or vacuum, may efficiently transport tissue specimens axially to a transfer magazine at the proximal end of the device 10.

According to one embodiment, flush may be incorporated in the annular space between an outer sheath (which may actually take the form of either a distal sheath 590 or an outer sheath) and inner sheath(s), to facilitate tissue transport. Vacuum may be drawn within the central lumen of a whole tubular coring and transport assembly 11, to facilitate tissue transport as well as flush fluid transport. This enables an operator to collect any fluids from the penetration and biopsy sites during the procedure in order to help with visualization under various guidance modalities and to collect cells for cytological analysis. Moreover, according to one embodiment, such a flush pathway enables the delivery of, for example, biologically active substances and/or markers.

Coupled with flush and vacuum, fenestrations defined in a proximal sheath and a distal sheath may enable a helical "pumping" feature and create a reservoir of fluids surrounding the tissue, which may enable a swirling wave action to interact with the cored and severed tissue samples to gently push them in the proximal direction. Such fenestrations may also lessen respective wall surface areas of these structures and thus decrease the surface friction experienced by the cored and severed tissue sample. Such structures also exhibit a favorable "sealing" effect surrounding the tissues, particularly where irregular tissues might, based on their own surface architecture, engender vacuum leaks. Indeed, the gentle urging of such transportation of the cored and severed tissue samples preserves the underlying tissue architecture and delivers a clinically-useful sample (e.g., one whose tissue architecture has not been unacceptably damaged during its transport) to, for example, a transfer magazine 27.

Figure 15:
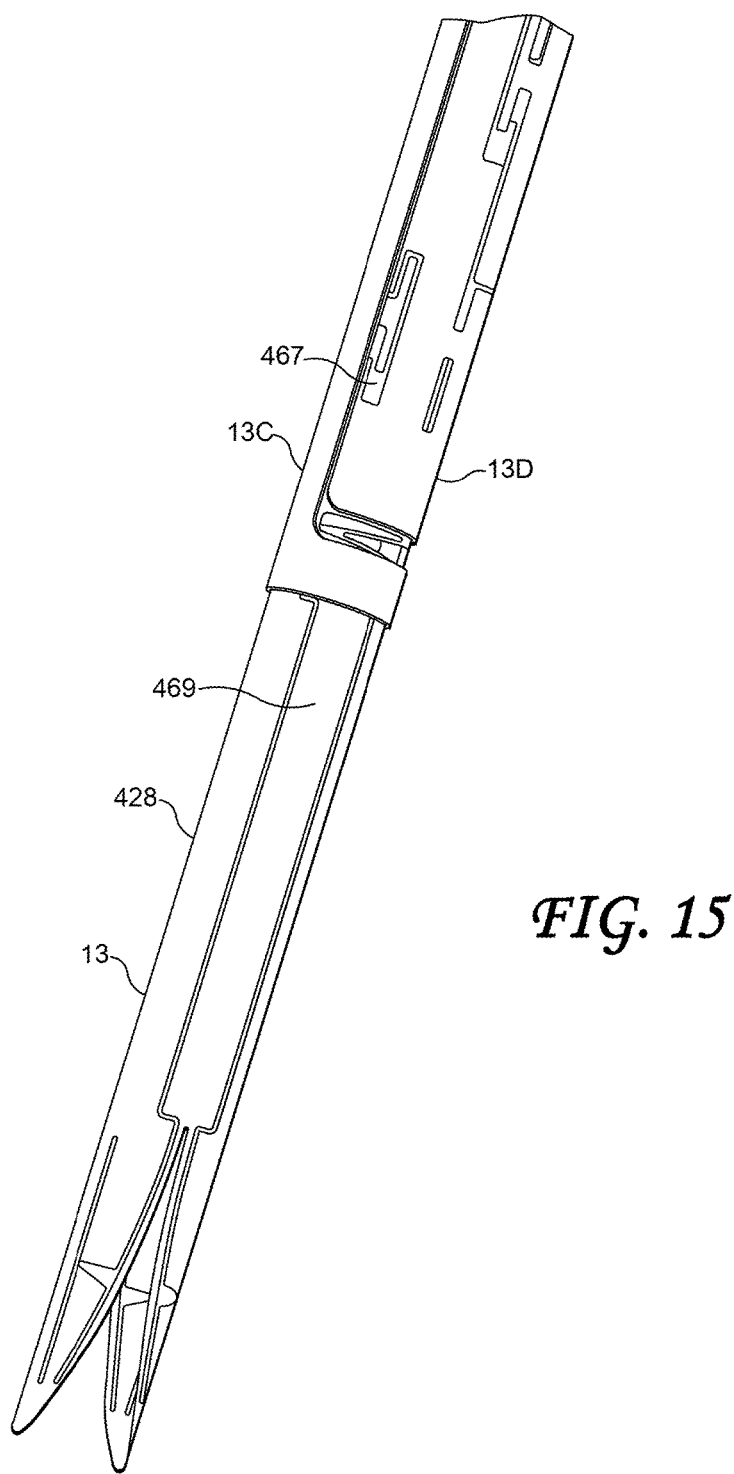
FIG. 15 shows the distal portion of an excisional device according to one embodiment.

FIG. 15 is a side perspective view of a single split tube actuating and rotating a work element 13, in yet another embodiment. In this embodiment, proximal and distal sheaths previously discussed may be replaced by a single tube, split along its long axis and incorporating travel limiting shapes (similar in functionality to element 467 of FIG. 2B, although located differently) along the split length of the tube. These travel limiting shapes are shown in this figure as T-shapes, but other shapes may be selected or envisioned. As shown, the distal end of one half, arbitrarily, the upper half 13C of the split tube may be attached to a tendon actuation member 469 while the distal end of the opposite (lower) half 13D, as shown by the cutout, may be attached to a body portion 428 of a monolithic beak assembly 13. In such a configuration, one half of the split tube acts on tendons of beaks while the opposing half acts on a body portion of a beak assembly or work assembly, thus allowing for axial movement between the upper and lower halves to constitute an actuation mechanism for opening and closing beaks as well as rotation, since the upper and lower halves of such a split tube necessarily rotate in synchronicity. An expansion chamber section proximal to a work assembly attachment point that was discussed above would be present in such an embodiment. Furthermore, such axial movement may be limited, in embodiments, by T-shaped or otherwise shaped tabs that may be formed as part of one or both tube halves sliding within travel limiting slots 467 in an opposing half of a split tube, according to one embodiment. Several of these tabs and slots may be arranged along the length of a split tube. Additionally, slot(s) 467 may be filled with a flexible substance, such as silicone, that may also be provided with a small hole that will open and close as a T-shaped tab moves axially in the slot. According to embodiments, this may allow flush fluids drawn between an outer sheath 330 and a split tube inner element to selectively pass into the central lumen of such a split tube to aid in tissue specimen transport.

According to one embodiment, an entire assembly of split tube, beak, living hinge and tendons may be formed of a single tube that may be, for example, laser cut (not shown, but easily envisioned wherein the lower half, for example, continues to become the body portion of a beak assembly and the upper half of the split tube continues to become a tendon actuating member, or vice versa). In the two embodiments discussed under this figure, only two tubes (outer sheath and inner split tube) are nominally present, and there may or may not be any helical elements at all associated with such embodiments.

Based upon the principles of distal work element (beaks) operations from the previous FIGS. 2 through 15, it may be seen that, according to embodiments, a rotating proximal sheath 584 or 300 (according to figures) may serve to both rotate a single beak or multiple beaks, as well as provide the mechanism for opening and closing such beak or beaks, by being itself moved axially distally such that its distal end pushes up against a non- or differentially-rotating distal sheath 590 or 320, or according to embodiments, such as of FIG. 13, by relative axial movement between a proximal sheath and a distal sheath, all configurations and embodiments of which for this device 10 are referred to as a tubular coring and transport assembly 11 in FIG. 1. In the inner lumen of this coring and transport assembly 11, a first helical element 582 may be provided to aid in tissue specimen transport proximally, which may be further aided or replaced by liquid flush introduced into the central lumen at the distal end of an assembly 11 and/or vacuum introduced at the proximal end of device 10. If provided, a first helical element 582 may rotate at a different speed than that of a proximal sheath and a beak element(s) 13. With these principles in mind, the following set of figures addresses the mechanical means of providing such actions to the distal end of device 10 of FIG. 1, according to embodiments. It may also be seen that the mechanical arrangements described herein are not the only arrangements that may accomplish all of these desired actions on a tubular coring and transport assembly 11, and other arrangements that may be envisioned by one skilled in the art are considered within the scope of this invention. It may also be envisioned that elements such as a first helical element 582 may be deleted, according to embodiments, but may still be illustrated in FIG. 16 below to show how it or they may be integrated into a device 10, if desired.

Figure 16:
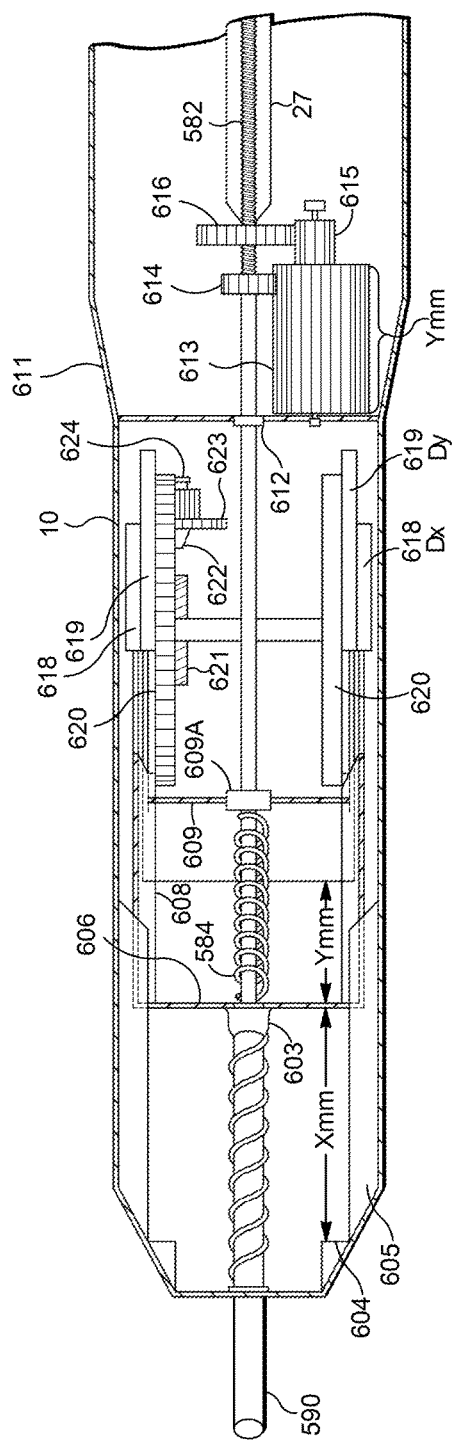
FIG. 16 shows a top view of a mechanical arrangement for cutting element rotation and actuation, according to embodiments.

FIG. 16 shows a top view of a mechanical arrangement for a tubular coring and transport element 11 rotation and actuation, according to one embodiment. From the left or distal side, a proximal end of a distal sheath 590 passes through a front seal 602, which in this view is at the distal end of a housing or handle portion 12 of device 10 (an outer sheath 330 is not shown in this view but may be present according to embodiments). A distal sheath 590 is free to move against an internal spring axially forward and back, the total distance of such movement being approximately equal to a maximum automatically or semi-automatically obtained sample tissue length (not to scale). At its proximal end, a distal sheath 590 is bedded into a tube socket/seal 603, which is itself attached to the forward wall of a distal sheath carrier 606, which slides back and forth within a slide 605 to a maximum distance defined by a carrier stop 604, both of which are formed in the outer housing of device 10 in this embodiment. Continuing to the right of the illustration, a proximal sheath 584, contained within a distal sheath 590 and rotating independently of it, may be seen passing through a thrust bearing 609A in the forward wall of a proximal sheath carrier 609, which itself slides axially inside a distal sheath carrier on a slide 608, and which is furnished with its own spring which effectively allows a return force to separate the two carriers if they are pushed together, which causes a proximal sheath to move backward or forward, respectively, in relation to a distal sheath. Recalling that it is the differential axial movement between a distal sheath and a proximal sheath that activates beak opening and closing, it may be seen that in this embodiment, such axial movement may be accomplished by the action of the two carriers in relation to one another. The total distance travelled by proximal sheath carrier 609 therefore relates to the axial distance travelled between a proximal sheath and a distal sheath to open or close a beak or beaks 13 at the distal end of device 10 according to embodiments.

A proximal sheath 584 is also free to move forward and backward, axially, under rotation as a result of a thrust bearing 609A described above. A proximal sheath 584 continues proximally in this illustration through a vacuum seal 612 at the forward bulkhead of a vacuum chamber 611, which serves to capture any stray fluids that are not aspirated through the central lumen of a whole tubular coring and transport assembly 11 or through a transfer magazine 27. Rotational force for a proximal sheath 584 is provided by its gear 614, in this illustration, which is driven by a proximal sheath pinion gear 613. Also in this illustration may be seen a first helical element 582, which may be driven at a different rotational speed than that of a proximal sheath by its own gear 616 and pinion gear 615, which may also drive a vacuum system (not shown) of the present biopsy device. If such is provided, a first helical element may terminate within a transfer magazine 27 in which tissue samples may be deposited as a result of device 10's action.

This illustration also shows that, according to one embodiment, the distal and proximal sheath carriers may terminate proximally by vertical side walls of any shape, and upon which a rotating dual cam gear 620, with individual cams such as a distal sheath cam 618 and a proximal sheath cam 619 acting upon the vertical side walls of the two carriers. The inner side walls and cam 619 correspond to a proximal sheath carrier 609 and the outer side walls and cam 618 correspond to a distal sheath carrier 606. It may be envisioned that, depending on the side profile of each cam as well as the side profiles of the two vertical side walls, many different tunings may actuate the same or differential movement, acceleration and timing of differential movement of the two carriers relative to each other, and thus to the combined and coordinated action of a distal work element of device 10, according to embodiments. For instance, at the beginning of the rotation of twin gear cams 620 with their individual cam elements 618 and 619, the carriers may be actuated equally, corresponding to forward movement of a distal sheath and a proximal sheath, thus coring tissue with beaks open and rotating. Upon reaching a certain axial distance, a cam 619 may continue forward, closing the beaks and keeping them closed while both distal and proximal sheaths retreat proximally carrying the tissue sample backwards and delivering it to a transport mechanism for eventual delivery to, for example, a transfer magazine 27. In such an embodiment, gentle traction would be applied to the tissue sample taken at the end of the part off stage of the biopsy device 10's action for that sample, further ensuring a positive part off from surrounding tissue. Many different cam/cam follower (vertical rear walls of the carriers) configurations or shapes may be envisioned to provide forward and backward axial movement combined with differential acceleration of individual sheaths to allow the device 10 to accomplish its desired operations at different pre-, intra-, and post-operative stages of penetration, coring, part-off, retrieval and storage of sequential samples, as well as material collection from or delivery to the target site as described previously. For instance, a dimple in the center vertical section of an inner carrier vertical rear wall would result in a double closing of beaks after a short time interval, which may result in further aiding positive part off of the tissue sample. The vertical walls of each carrier may be asymmetrical to each other or in their upper or lower sections, depending on the mechanical effect desired. The cams themselves may be asymmetrical in their individual side shapes, which combined with special shapes imparted to the vertical rear walls of the carriers could result in extremely fine tuning of carrier axial movements at any desired point in time, defined by the revolution speed and instantaneous radial angle during revolution of twin cam gears at any time. Twin cam gears of this embodiment may be powered by a worm gear 621, which would allow for movement of the two carriers to be frozen in position at any desired stage. A worm gear 621 is itself driven by a pinion gear 623 operating through a simple clutch mechanism 622. It should also be noted that at any time, carrier 609 and carrier 606 may be manually squeezed together through a simple mechanical linkage (not shown), which may cause beaks to close and part off or remain closed at an operator's choice. It should also be noted that rotation and axial movement are independent of one another with such an arrangement, and thus may be controlled with different actuation mechanisms to allow the device 10 to accomplish all of its intended functions. Again, this illustration is only one of many different mechanical arrangements that may be envisioned by one of skill in the an, all of which are considered to be within the scope of this disclosure, and that may be selected to enable the device to accomplish any or all of the following actions considered characteristic of device 10, according to embodiments:

Penetration to the target tissue site or withdrawal from the site:
  Beak(s) closed, no rotation
  Beak(s) closed, with rotation
  Beak(s) open, no rotation
  Beak(s) open, with rotation;
Semi-automatic tissue sampling (gear cams stop after one rotation);
Automatic tissue sampling (gear cams continue to rotate until interrupted);
Short core sampling (using the manual part off function described above); and
Continuous core sampling of any sample length, terminating in manual part off.

Figure 17:
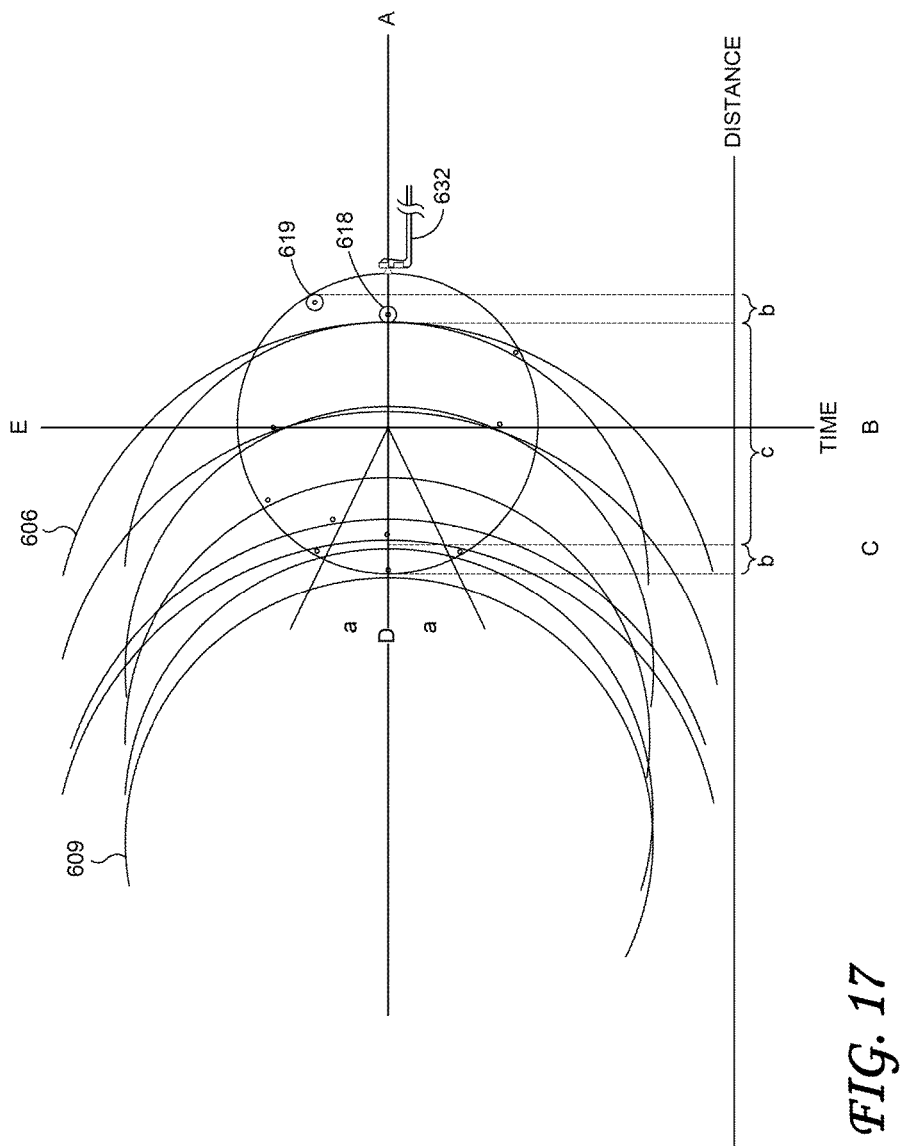
FIG. 17 is an illustration of a cam and cam follower arrangement, according to embodiments.

FIG. 17 is an illustration of principles of a different arrangement of a cam gear and cam follower arrangement, according to embodiments. This figure specifically looks at the time based action of a geared cam 620 but with two pins surrounded by bushings that act in a similar manner to cams 618 and 619 from FIG. 16, and are thus labeled as such in this figure. In this embodiment, a geared cam wheel 620 is assumed to rotate in a clockwise direction, with pin 618 (analogous in function to cam 618 of FIG. 16) being a short pin that acts only on the inside of proximal sheath carrier's vertical rear wall, and pin 619 (analogous in function to cam 619 of FIG. 16), which is a longer pin that is capable at times of effectively acting on both a proximal sheath carrier 609 and a distal sheath carrier 606 vertical rear walls simultaneously. The arc distance between the two pins on the inner surface of a gear cam wheel shown by the two angles "a", using the analogy from FIG. 16, determines which of the two pins is acting on which carrier at any given point in time, either together or in a lead-lag relationship depending on the revolution position in time of the gear wheel as it rotates. For purposes of illustration, the larger arcs scribed in this figure correspond to the vertical rear wall surface of a distal sheath carrier 606, and the smaller scribed arcs correspond to the vertical rear wall of a proximal sheath carrier 609. The pins 618 and 619 are shown with their bushings only at the start of the cycle, for purposes of illustration, and are shown as dots at various other locations which correspond to their movement at various time intervals with gear cam wheel 620. A gear cam wheel 620 is shown to the right of the figure, with the arcs of the carriers extending to the left to correspond with the independent carrier movement outlined in the previous FIG. 16. It can be seen that the longer pin 619 is a shorter radial distance from the center of a gear cam wheel 620 than the short pin 618, which pin 618 acts only on a proximal sheath carrier 609. It is also lagging the long pin 619 in revolutionary time, which implies that it comes into play only at a certain point in the clockwise movement of a gear cam wheel 620. Recalling that if a proximal sheath carrier is pressed farther distally than a distal sheath carrier at any time (even manually by the operator), the beak(s) will tend to close, following the principles outlined in previous figures, at a certain point in time (at approximately the 8 o'clock position in this figure) the short pin will begin to act independently on a proximal sheath carrier and extend it differentially farther distally than a distal sheath carrier, closing the beak(s) and keeping them closed until that point in time (at approximately the 2 o'clock position in this illustration) when the beak(s) will again open in anticipation of another forward excursion of both proximal and distal sheaths for coring and sampling.

For purposes of illustration, it is assumed that the rest position of the two carriers is when a long pin 619 is in the 3 o'clock position. In this position, beak(s) are open (labeled as "A" or zero time in terms of rotation time) and both distal and proximal sheath are at their closest proximal point to the housing of biopsy device 10. FIG. 17 includes a small microswitch 632 with a pointer on a gear wheel, whose function could be to stop/restart gear wheel 620 revolution when a long pin 619 is in its starting 3 o'clock position, which action may correspond to the difference between semi-automatic (one revolution and microswitch stops revolution until disabled/re-enabled) and fully automatic (microswitch disabled altogether and thus rotation and sampling continues until operator interruption of the process) sampling action of the device 10, according to embodiments. The total excursion time of the distal end of the device 10 (coring forward, part off, sample retrieval and transfer to the transport mechanism, return to starting position) occurs in a single revolution of a gear cam 620, and the individual actions of pins on individual sheath carriers 606 and 609 are as described herein. Such total sample (excursion) time may vary from as little as 2 seconds to as long as 12 seconds, depending on embodiments, with a nominally designated time of 4 seconds, in one embodiment. If the total time for rotation is assumed to be 4 seconds, then rotational position "A" corresponds to zero, position "B" corresponds to one second elapsed time, position "C" corresponds to that interval when the short pin takes over and the beak(s) begin to close, position "D" corresponds to two seconds elapsed time (and wherein the beak(s) have closed completely as a short pin 618 reaches that position), position E corresponds to three seconds elapsed time, and the return to position A corresponds to four seconds total rotation time, assuming constant speed of gear cam wheel 620, which may also be variable, according to embodiments. When a long pin is at the 3 o'clock position, it is acting on the vertical rear wall edges of both carriers simultaneously, which continues to be the case until the long pin 619 has reached approximately the 9 o'clock position, at which time a short pin 618, lagging behind at a calculated arc distance "a" and further radially than the long pin, will start to engage only an inner proximal sheath carrier vertical rear wall, continuing its forward travers at the moment when a distal sheath carrier has ceased its maximum forward or distal movement. The result is that the beak(s) will close, and remain closed until the long pin reaches approximately the 1 o'clock position, thus withdrawing the sample under either continuing proximal sheath rotation or not, as desired (since rotation action of the proximal sheath, which rotates the beak(s) and forward/rearward excursion of the carriers are independent of one another, as illustrated in FIG. 16). As a long pin 619 reaches the 3 o'clock position, the beak(s) are fully open and ready for coring forward again and parting off and transferring another sample to a transport mechanism and ultimately, for example, to a transfer magazine 27. Of note is that according to embodiments, sampling cycle time is a function of the time of one revolution of a gear cam wheel 620, and that the timing for beak actuation is a simple function of the placement of short pin 618 in relation to long pin 619. The arched (in one embodiment) configuration of carrier vertical rear walls is only one configuration, but different profile shapes of each vertical rear wall will tend to accelerate or decelerate the actions of the pins on those surfaces, and many different vertical rear wall profile shapes are possible, depending on embodiments. Additionally, the profile shapes of vertical rear walls of carriers may differ from top to bottom to impose time based factors on the action (axial movement, with implied beak actions associated with such excursions of the two carriers, in relation to one another) of each individual carrier 606 or 609, according to embodiments. Finally, in this illustrated embodiment, the axial distance horizontally between a short pin 618 and a long pin 619 corresponds to the axial relative distance (and therefore time) necessary for travel of a proximal sheath carrier 609 compared to a distal sheath carrier 606 in order to accomplish beak(s) closure (shown as "b" in this figure as shown and discussed in FIGS. 5, 7 and 8 above.) Total excursion distance of the distal end of device 10 is shown as "c" in this figure, and is a function of the placement of pins 618 and 619 and the diameter of a gear cam wheel 620, in one embodiment. Such total excursion distance may be of any length desired, according to embodiments, and for one embodiment, such distance is nominally 1 inch or 2.54 centimeters, corresponding to maximum automatic sample length. Again, it should be noted that samples of any length may be obtained by the operator with device 10, as will be discussed further below.

Figure 18:
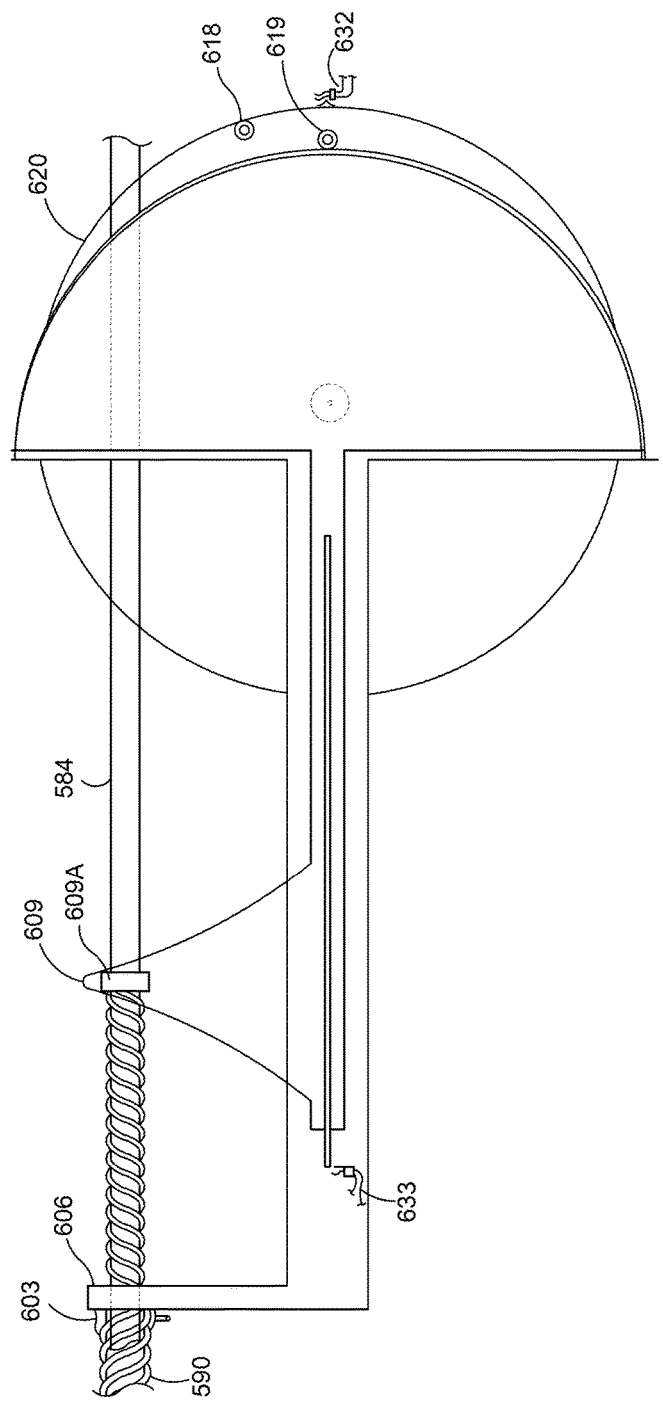
FIG. 18 is a side view of a cutting element actuation mechanism, according to embodiments.

FIG. 18 is a side view of a cutting element actuation mechanism consisting of twin inner and outer sheath carriers, such as 606 and 609 of FIG. 9, according to embodiments. From the preceding FIGS. 9 and 10, it may be seen that rotation of gear cam wheel 620 will slide both carriers axially distally and proximally, in differential movement to each other as previously described. Also shown in this figure is a distal sheath 590 with its external return spring, a distal sheath socket and flush connection 603, a proximal sheath 685, a proximal sheath thrust bearing 609A, a gear cam wheel 620 with its short bushed pin 618 and its long bushed pin 619, a gear cam wheel microswitch 632 and a maximum forward travel proximal sheath carrier microswitch 633. In the embodiment shown in this figure, the vertical rear walls of each carrier 606 and 609 are profile shaped as hemi-circular in form and of nearly the same size, although other embodiments may alter the shapes of either carrier rear vertical wall to be of any shape desired, which will affect the action of the two carrier's axial movements, according to embodiments. The rear walls may have special features, such as elliptical shapes in their upper or lower halves, dimples, wavy shapes or any other shape desired, and one skilled in the art will recognize that such profile features will act with the pins of a gear cam wheel to accelerate or decelerate the individual axial movements of the two carriers in relation to each other, all such designs and corresponding movements of which are considered to be within the scope of this invention. Further, the profile shape of each of the two carriers may differ from each other, and the rear walls may be lowered in relation to the long horizontal axis of each of the carriers, resulting in a cantilevered action on the carriers as imparted by a gear cam wheel 620. This may be especially important for embodiments of device 10 specifically designed for stereotactic table use, where keeping the coring and transport assembly 11 of FIGS. 1 and 19 as near as possible to the upper end of the device may be of benefit in allowing a "down the barrel" view of the device in action, as well as for imaging mechanisms where such a benefit has use in being placed as closely as possible to the long axis of the working end (distal end) of the biopsy device, according to embodiments. According to other embodiments, the two carriers and cam wheel may be replaced by thrust bearing carriers with pins that intersect the slots in a barrel cam, or that may be connected to connecting rods and a crankshaft, for example, and any of these or other mechanical arrangements designed to allow rotation, relative axial movement between a proximal and distal sheath, and forward excursion of a tubular coring and transport assembly may be envisioned by one skilled in the art and are therefore considered to be within the scope of this disclosure.

Figure 19:
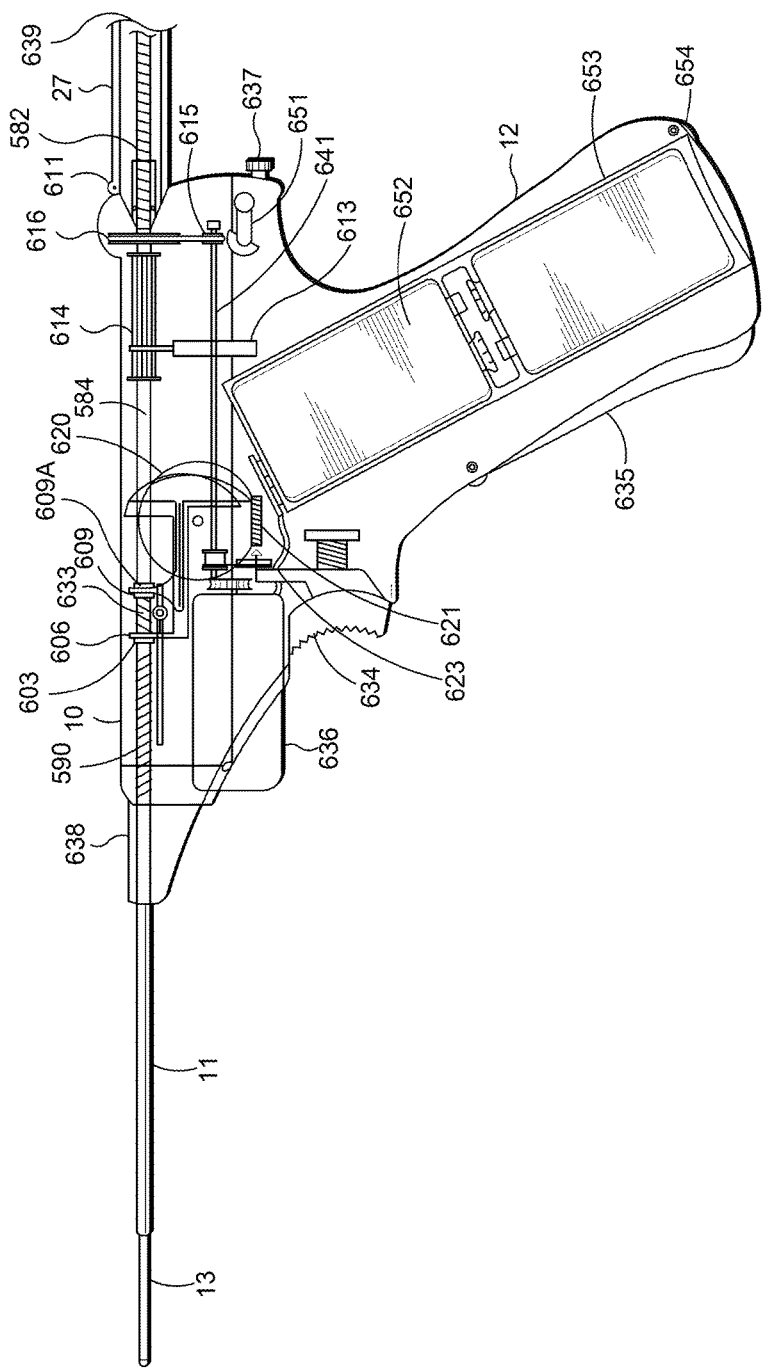
FIG. 19 is a side view of internal and external features of a biopsy device.

FIG. 19 is a side view of internal and external features and elements of a biopsy device 10, according to one embodiment. In this figure, the mechanism of a distal sheath carrier 606 and proximal sheath carrier 609 with their elements of FIGS. 16, 17 and 18 are shown in near scale size, according to embodiments. Other elements also shown in various previous figures herein include a tubular coring and transport assembly 11, a non- or differentially-rotating distal sheath 590 (320), a work element 13, a proximal sheath 584 (300), a distal sheath carrier 606, a proximal sheath carrier 609, a proximal sheath thrust bearing 609A, a distal sheath socket/flush port 603, a proximal sheath pulley 614 (analogous to gear 614 of FIG. 16, as will also apply to other pulleys in this figure, which correspond to various gears of FIG. 16), a first helical element pulley 616, a vacuum chamber 611, a first helical element or transport helix 582 (which may be deleted, according to embodiments), a transfer magazine 27, a flush port 638 (which may be located at either end of handle portion 12), an aspiration/material delivery port 639 (not shown in this view but located at the proximal end of device 10 as indicated herein), a rotation power switch/led indicator 635, a DC adapter port 637, a DC motor 636, a transport helix pinion pulley 615, a proximal sheath pinion pulley 613, a worm gear clutch pinion pulley 623, a worm gear clutch 624, a worm gear clutch (gear cam wheel clutch) button 634, a worm gear pinion 621, a gear cam wheel 620, a drive mechanism carrier common driveline 641, a manual part off button 633, batteries 652 in a battery carrier 653 and a battery carrier release lever 654. Also shown is that the top section of the device 10 may be detached along with the distal end of the device and exchanged for a new entire top section, being secured by latch 651, according to embodiments. It should be noted that, according to embodiments, many other substitutions for any or all of the elements noted herein that accomplish the same function or functions may be visualized by one skilled in the art, and all such substitutions are considered within the scope of this invention. It should be noted that according to embodiments, rotation of a proximal sheath, first helical element, and distal sheath (if rotated) or outer sheath (not shown) may be independent of the distal and proximal axial movement of a tubular coring and transport assembly 11, and because of that feature, according to embodiments, the operator may select various functions of the device 10 at any time, as described previously under FIG. 16 above.

Further aspects of the use of a transfer magazine 27 (also shown in FIG. 1) are now described, such that various clinical needs may be fulfilled by permitting the operator of the present biopsy device to inspect the core samples more closely, and in some cases tactilely, without destroying the record keeping function of a transfer magazine 27. Additional methods of ex-vivo imaging are also described, as are the samples in the order in which they were collected and stored within a storage/record keeping transfer magazine 27, according to still further embodiments. Since a transfer magazine, according to embodiments, may be configured to be removable and/or replaceable at any time(s) during the procedure, the present biopsy device enables a variety of procedural methods to ensue which would not be possible, or at least would be impractical, without the structures disclosed herein. For example, using the present biopsy device, a clinician may segregate the contents of one transfer magazine from the contents of another, additional transfer magazine. The operator of the present biopsy device may also have the ability to interrupt coring/transport/storage with another function of the biopsy device, all the while, at operator's discretion, keeping the present biopsy device's shaft coring and transport assembly 11 in place, thus minimizing trauma associated with repeated removal from the body and insertion of these elements of the present biopsy device.

Indeed, according to one embodiment, a tissue biopsy method may comprise performing coring/biopsy/transport cycles as described above. Thereafter, removing the transfer magazine and/or proceeding to marking and/or treatment phases may complete the procedure. The transfer magazine may then be removed and, if desired, placed under X-Ray, magnetic resonance imaging and/or ultrasound transducer or high-resolution digital camera if the transfer magazine is made of a transparent material. The core tissue specimens may then be imaged and/or recorded. The magazine may then be placed in a delivery receptacle, sealed and delivered to a lab for further analysis, making note of core lengths and correlating with imaging record(s) in-situ and ex-vivo. Upon removal of transfer magazine from the present biopsy device, the collected cores may then be visually inspected through the transparent walls of the magazine. The magazine may then be split open to tactilely analyze the tissue specimens as desired. The magazine may then be closed again, with the specimen therein. The magazine may then be deposited in a transport receptacle, sealed and delivered to a lab.

The transfer magazine may then be replaced with additional empty transfer magazine(s) as needed to complete tissue collection during the biopsy procedure. Alternatively, other cartridges/adapters or magazines may be fitted to the present biopsy device to deliver, for example, medications, markers and/or tracer elements, therapeutic agents, or therapeutic and/or cosmetic implants to the biopsy site. The procedure may then be terminated or continued, such as would be the case should the practitioner desire to biopsy/core other nearby areas as deemed clinically useful.

As shown in this figure and previous figures, a device 10 with a small diameter distal end may be gently placed in proximity to or through a lesion, or may be forward fired through the lesion using the internal mechanism of device 10, in embodiments. Clinically and procedurally, the ability of a biopsy device to advance gently towards a target lesion provides several advantages. Indeed, when a biopsy device does not advance gently toward a target lesion or does not smoothly core through dense target tissue, the operator may be led to exert excessive force onto the biopsy device, thereby potentially forcing the biopsy device into and even through adjacent structures. There have been instances of biopsy device components being broken off, requiring surgical removal thereof from the biopsy site when excessive force was needed in attempts to obtain core samples from tissues such as dense breast tissue. The present method of introducing a small diameter distal sheath, with the withdrawn and closed beak(s) as a penetration mode in one embodiment herein and provided for with a specific cycle stage in the biopsy device 10 of FIG. 1, enables an operator to gently and smoothly approach a target lesion without requiring excessive manual axially-directed force to be exerted on the present biopsy device by the operator or the stereotactic table itself, if used. It is to be noted that when excessive force must be exerted to advance conventional coring devices through dense tissue, the resultant image provided by guidance modalities may be significantly distorted by the force applied to the conventional coring device and transferred to the surrounding tissue which may cause the resultant image to be less distinct or blurred, and which, in turn, makes the biopsy procedure less accurate and much more difficult technically. This force may also damage tissue, resulting in loss of tissue architecture and production of the aforementioned biopsy artifact. It is an important goal of all core biopsy procedures to firmly establish that the core sample is taken from the highly specific image area, notwithstanding the constraints imposed by the small dimensions of the target tissue. Such small dimensions, therefore, require clear views of sharp margins to attain the kind of accuracy required during a biopsy procedure.

Flush mechanisms may be incorporated into the biopsy device 10, according to embodiments, to aid in tissue specimen transport to, for example, a transfer magazine 27. Such mechanisms may consist of a distal tube socket/flush port 638 or 603, which may deliver flush fluids to the distal end of the device between distal and proximal sheaths, for example. Flush fluids and other materials may also be delivered to the tissue site through the central lumen of the device, with beak(s) closed (as described for liquids under FIG. 2A above through living hinge slots) or open, using an aspiration port 639, according to embodiments. Flush fluids may also be delivered to the distal tip through ports in a collar 593 of a distal sheath shown in FIG. 6 above. As previously described, fluids, solids and other materials may be delivered to the tissue site through the central lumen of the device, and various slots and mechanisms such as the open beak(s) may be used in conjunction with flush fluids to gather and transport cells and liquids from the tissue site for later cytological analysis.

Significantly, the coring and transport mechanisms and methods described and shown herein are configured to apply traction while coring as beaks close against each other and are then withdrawn to their resting position, carrying the tissue specimen with them. That is, coring, cutting, parting-off, traction and transport may be, according to one embodiment, carried out simultaneously. In so doing, as traction is applied during a cutting event, the cutting event is not only rendered more efficient, but may be the only way to successfully cut certain tissue types. This traction, according to one embodiment, may be facilitated by the continuous interaction of a helical element(s), a tubular coring and transport assembly, and flush and vacuum, depending on embodiments, which all or separately act together to provide gentle continuous traction beginning immediately upon the tissue entering the lumen of a tubular coring and transport assembly 11 of FIG. 1, and continuing during part-off of the tissue specimen. According to one embodiment, the ratio between the twisting and pulling actions may be carefully controlled by, for example, control of rotation versus crank or cam speed, or other axial control mechanism. According to one embodiment, when a beak assembly is open wider than the inner lumen of a tubular coring and transport assembly, tissue may be drawn in by at least surface treatment(s), channels, and helical elements, past a sharp beak assembly and into the interior lumen of a tubular coring and transport assembly. This may be, according to one embodiment, augmented with either flush or vacuum or both. However, it is to be noted that the transport mechanisms and functionality described herein is more effective than vacuum alone, as vacuum predominantly acts locally at the proximal surface of a specimen. Indeed, transport mechanisms described and shown herein (e.g., surface treatments, rifling, swirling fluid pumps, vacuum slots, helical element(s), and the selective rotation of these) may be configured to act along the entire length of the outer surface of the tissue specimen, which may be essential for certain tissue types. Vacuum, according to one embodiment, may well augment such traction and transport but need not be the primary modality be which tissue specimen are drawn proximally or materials are pushed distally to the target lesion site. According to one embodiment, vacuum may be primarily used for extracting cells, body fluids and flush fluids, and to prevent the inadvertent injection of outside air, which can obscure an ultrasound image or transfer other unwanted elements into the body.

Figure 20:
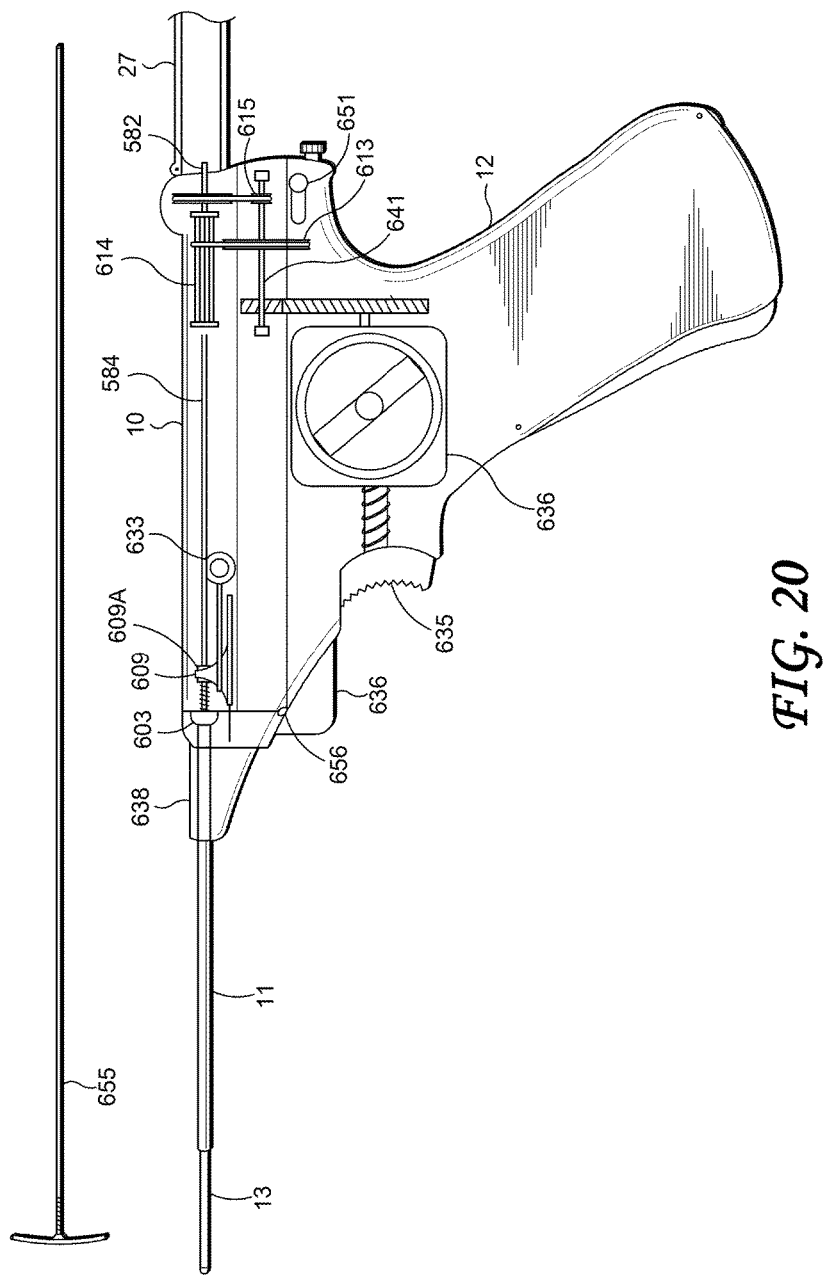
FIG. 20 is a side view of internal and external features of a simplified embodiment of a biopsy device.

FIG. 20 represents a device 10 with simplified internal mechanism and controls, according to embodiments. Although this device 10 as shown in this figure has few internal moving parts, it is still capable of all of the functions listed above under FIG. 16 above with the exception of semi-automatic and automatic sampling. Indeed, while much of the device as shown in the embodiment of this figure is designed for manual operation (including a wind up motor 636 and simplified drive train providing rotational movement to a proximal sheath 584 and thus beaks 13 and a first helical element 582), the configuration of distal end embodiments of the device 10, as shown in the previous figures, allows for forward and backward movement to be a function of operator action to position the device as a whole, and for the device's function of single insertion/multiple samples to be realizable. The elements shown in this figure include the device 10, a tubular coring and transport assembly 11, a work element 13, a flush port 638 which may be connected to a simple drip bag of saline solution as well as a (for example) drug/anesthetic delivery tube (not shown), a distal sheath socket 603, a proximal sheath carrier 609 with a thrust bearing 609A, a proximal sheath 584 and a first helical element 582, a transfer magazine 27, a start/stop rotational power switch 635 (note that its placement is different for a simplified device 10 than that shown in FIG. 19, for example) and a detachable upper unit of the device engaged at pivot point 656 and locked down by latch 651 to a handle portion 12, thus engaging the motor pinion gear to the driven gear powering a common driveline 641. Also shown is a manual part off button 633, which allows an operator to open or close beaks at any time, with or without rotation of the proximal sheath/first helical element (if the latter is used). Thus this simplified device may serve a useful purpose in developing countries, for example. A transfer magazine 27 may serve as a port for vacuum (not shown), if used, or for delivery of materials to the tissue site within the body down the central lumen of this simplified device, according to embodiments. If a first helical element is not used, along with any fluid flush or vacuum, the tissue sample may simply be accumulated in a proximal sheath and eventually pushed back into a transfer magazine 27 by means of a rod 655 at the end of a procedure. Different embodiments of a simplified device may incorporate additional internal and external features of the device 10 of this invention, including for example a simple electric motor and rechargeable batteries, some of which are shown in FIG. 19 above, and as described herein.

The present biopsy device may be formed of or comprise one or more biocompatible materials such as, for example, stainless steel or other biocompatible alloys, and may be made of, comprise or be coated with polymers and/or biopolymer materials as needed to optimize function(s). For example, the cutting elements (such as the constituent elements of a beak assembly 13) may comprise or be made of hardened alloys or carbon fiber and may be additionally coated with a slippery material or materials to thereby optimize passage through living tissues of a variety of consistencies and frictions. Some of the components may be purposely surface-treated differentially with respect to adjacent components, as detailed herein in reference to a transporting tubular and storage component. The various gears or pulleys may be made of any suitable, commercially available materials such as nylons, polymers such as moldable plastics, and others. If used, the motor powering the various powered functions of the present biopsy device may be a commercially available electric DC motor. The handle portion of the present biopsy device may likewise be made of or comprise inexpensive, injection-molded plastic or other suitable rigid, easily hand held strong and light-weight material. The handle portion may be configured in such a way as to make it easily adaptable to one of any number of existing guiding platforms, such as stereotactic table stages. The materials used in the present biopsy device may also be carefully selected from a Ferro-magnetic standpoint, such that the present biopsy device maintains compatibility with magnetic resonance imaging (MRI) equipment that is commonly used for biopsy procedures. Vacuum/delivery assembly components may comprise commercially available vacuum pumps, syringes and tubing for connecting to the present biopsy device, along with readily available reed valves for switching between suction and emptying of materials such as fluids which may be suctioned by vacuum components. The fluids collected by the embodiments of the present biopsy device in this manner may then be ejected into an additional external, yet portable, liquid storage vessel connected to the tubing of the present biopsy device, for safe keeping for laboratory cellular analysis.

The power source may comprise an external commercially available AC to DC transformer approved for medical device use and plugged into the provided socket in the present biopsy device, or may comprise an enclosed battery of any suitable and commercially available power source. The battery may be of the one-time use disposable (and optionally recyclable) variety, or may be of the rechargeable variety. Additionally, other power sources, including mechanical motors or linkages, compressed air or hydraulic motors may be used.

The cutting beak assembly of embodiments of the biopsy devices may be used, without alteration of their shape, attachment or any other modification, to penetrate tissue on approach to a target lesion. The cutting beak assembly may then be used to open and core the tissue specimen, and to thereafter part-off the specimen at the end of the coring stage. The beak assembly may also be used to help augment transport of the collected specimen. Having such multiple functions integrated in a single device saves valuable cross-sectional area, which in turn creates a device that has a minimal outer diameter while providing the maximum diameter core sample. Maximizing the diameter of the core sample is believed to be significant from a clinical standpoint, since it has been demonstrated in multiple peer-reviewed journals that larger diameter core specimens yield more accurate diagnoses. The clinical desire for large diameter core samples, however, must be balanced against the trauma associated with larger caliber devices. Embodiments of the present biopsy device optimize the ratio so that the clinician can have the best of both worlds. Advantageously, according to one embodiment, an internal helical transport system may be configured to augment the coring function of the forward cutting beaks. Helical transport coring elements may be configured to apply gentle, predictable traction on the cored specimen, during and after coring, which permits pairing the ideal speed of longitudinal excursion of the coring elements of the present biopsy device with the ideal speed of rotational movement of the same elements. In this manner, the architecture of the collected specimen is less likely to be disrupted during transport. It has been shown in peer-reviewed scientific articles that preserving tissue architecture (i.e., preserving the architecture of the tissue as it was in vivo) to the greatest extent possible facilitates a more accurate diagnosis. A vacuum/delivery mechanism may be configured to enable the force of vacuum to be exerted directly to the coring transport components, such that coring and transport of the specimen is handled as delicately, yet as surely, as possible and comprises non-significantly dimension-increasing components such as progressively sized fenestration features within tissue collection areas. If the present biopsy device were to rely solely on vacuum for tissue transport, then vacuum artifact, which is a known and described phenomenon associated with conventional biopsy devices, might be present to a greater degree than is present (if at all) in embodiments described herein. On the other hand, were embodiments of the present biopsy device to rely solely on a physical pushing or pulling mechanism to retrieve cut specimen samples, crush artifact might be more prominent than is otherwise present when embodiments of the present biopsy device and methods are used.

The internal surface treatments of an outer tube and a hollow, helical inner component, when acting in concert; transport materials of a variety of phase states longitudinally without the need for complex components that would otherwise contribute substantially to the outer caliber dimensions of the present biopsy device. Embodiments comprise a hollow helical transport mechanism that may be both strong and flexible, and which continues to function even when distorted by bending. Conventional biopsy devices typically cease to function properly if distorted even slightly. As such, the present biopsy device may be configured to define a curve along its longitudinal axis and in this case would still function properly, with minimal modifications.

Advantageously, a biopsy and coring device, according to embodiments, comprises features configured to perform medical core biopsy procedures, or shaping procedures (such as for vascular applications) or harvesting tissue for other uses. These features comprise structures configured for penetration, coring, part-off, transport and storage of core specimens for medical purposes such as diagnosis and treatment of a variety of diseases and abnormalities. Integral and detachable components may be provided and configured to aspirate fluids for cellular analysis as well as deliver materials at various selectable stages of the procedure. The present biopsy device may be selectable for automatic and/or semi-automatic function, may be used with or without image guidance, and may be compatible with a variety of guidance imaging equipment such as ultrasound, magnetic resonance imaging and X-ray imaging. The present biopsy device may be configured to be disposable and/or recyclable, highly portable, and delivered for use in sterile packaging, typical of medical devices having contact with internal body structures. The present biopsy device may be configured to be minimally invasive. As embodied herein, the present biopsy device comprises several features that may be therapeutic in nature, to be utilized at various stages along the diagnosis/treatment pathway.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

The invention claimed is:

1. An excisional device, comprising:
a proximal sheath;
a distal sheath;
a handle portion comprising a distal end and a proximal end, the handle portion comprising, disposed therein, a cam gear, a proximal sheath cam coupled to the cam gear and to the proximal sheath and a distal sheath cam coupled to the cam gear and at least to the distal sheath;
a cutting assembly comprising at least a first articulable beak, the cutting assembly being coupled to the distal end of the handle portion and configured to rotate, penetrate, core, part-off and at least one of transporting and containing parted-off tissue, the cutting assembly being configured to at least have a fully open configuration and a closed configuration, and to at least fit within the distal sheath in the fully open configuration and to extend out of the distal sheath in the closed configuration;
a tissue storing magazine coupled to the proximal end of the handle portion and configured to receive and store the parted-off tissue,
wherein the cam gear is configured to rotate, so that one rotation of the cam gear causes the proximal sheath to move distally relative to the distal sheath from a resting position and then causes the proximal sheath to return to the resting position while the cutting assembly, over the course of the one rotation of the cam gear:
rotates while advancing distally to at least partially extend out of the distal sheath;
cores tissue while rotating and advancing, parts-off a piece of tissue of a length determined by an amount of distal excursion of the cutting assembly within tissue,
rotates while retracting proximally to a position at least partially withdrawn into the distal sheath; and transports the parted-off piece of tissue toward the tissue storing magazine.

2. The excisional device of claim 1, wherein parted-off tissue contained in the cutting assembly are configured to be pushed into the tissue storing magazine by a push rod inserted axially within the cutting assembly.

3. The excisional device of claim 1, further comprising a manual part-off actuator, configured to cause the cutting assembly to part-off cored tissue from surrounding tissue.

4. The excisional device of claim 1, wherein the cutting assembly is configured to rotate under power from a mechanical wind-up motor within the handle portion.

5. The excisional device of claim 1, wherein cutting assembly is configured to rotate under power from an electrical motor within the handle portion.

6. The excisional device of claim 1, wherein the first articulable beak is configured to have the fully open configuration that is suitable for coring and the closed configuration that is suitable for at least one of parting-off pieces of tissue, penetrating tissue and for tissue dissection.

7. The excisional device of claim 1, wherein the cutting assembly comprises a single hypo tube in which cuts are made to form at least one articulable cutting element.

8. The excisional device of claim 7, wherein the at least one articulable cutting element is actuable to assume the fully open configuration and the closed configuration.

9. The excisional device of claim 1, wherein the handle portion comprises a lower portion and a detachable upper portion.

10. The excisional device of claim 9, wherein the detachable upper portion is pivotably coupled to the lower portion.

11. The excisional device of claim 1, wherein the cutting assembly is detachable from the handle portion.

12. The excisional device of claim 1, wherein the tissue storing magazine is detachable from the handle portion.

13. The excisional device of claim 1, further comprising a flush port provided in the handle portion through which at least liquids may be delivered and evacuated.

14. A method of excising tissue, comprising:
providing an excisional device comprising a proximal sheath; a distal sheath; a handle portion, the handle portion comprising, disposed therein, a cam gear, a proximal sheath cam coupled to the cam gear and to the proximal sheath and a distal sheath cam coupled to the cam gear and at least to the distal sheath; a cutting assembly comprising at least a first articulable beak, the cutting assembly being coupled to one end of the handle portion and configured to rotate, penetrate, core, part-off and transport or contain parted-off, the cutting assembly being configured to at least have a fully open configuration and a closed configuration, and to at least fit within the distal sheath in the fully open configuration and to extend out of the distal sheath in the closed configuration; and
a tissue storing magazine coupled to another end of the handle portion and configured to receive and store the parted-off tissue,
inserting at least the cutting assembly of the provided excisional device into tissue;

rotating the cam gear over one whole rotation and, during the course of the one whole rotation of the cam gear, sequentially:

causing the proximal sheath to move distally relative to the distal sheath from a resting position while the cutting assembly extends at least partially extend out of the distal sheath while rotating, advancing and coring through the tissue;

causing the proximal sheath to return to the resting position while parting-off a piece of tissue of a length determined by an amount of distal excursion of the cutting assembly within the tissue, and retracting the cutting assembly proximally to a position at least partially withdrawn into the distal sheath while rotating and transporting the parted-off piece of tissue toward the tissue storing magazine.

15. The method of excising tissue of claim 14, further comprising axially inserting and pushing a push rod within the cutting assembly to push the parted-off piece of tissue contained in the cutting assembly into the tissue storing magazine.

16. The method of excising tissue of claim 14, further comprising actuating a manual part-off actuator configured to cause the cutting assembly to part-off cored tissue from surrounding tissue.

17. The method of excising tissue of claim 14, further comprising winding up a mechanical wind-up motor within the handle portion to power the cutting assembly.

18. The method of excising tissue of claim 14, further comprising applying electrical energy to an electrical motor within the handle portion to power at least the cutting assembly.

19. The method of excising tissue of claim 14, wherein the providing step is carried out with the first articulable beak configured to have the fully open configuration that is suitable for coring and the closed configuration that is suitable for at least one of parting-off tissue and penetrating tissue.

20. The method of excising tissue of claim 14, wherein the providing step is carried out with the cutting assembly comprising single hypo tube in which cuts are made to form at least one articulable cutting element.

21. The method of excising tissue of claim 14, wherein the providing step is carried out with the at least one articulable cutting element being actuable to assume the fully open configuration and the closed configuration.

22. The method of excising tissue of claim 14, the providing step is carried out with wherein the handle portion comprising a lower portion and a detachable upper portion.

23. The method of excising tissue of claim 14, wherein the providing step is carried out with the detachable upper portion being pivotably coupled to the lower portion.

24. The method of excising tissue of claim 14, further comprising detaching the cutting assembly from the handle portion after a desired number of pieces of tissue are parted-off.

25. The method of excising tissue of claim 14, further comprising detaching the tissue storing magazine, with the tissue stored therein, from the handle portion.

26. The method of excising tissue of claim 14, further comprising delivering or evacuating a liquid through a flush port provided in the handle portion.

* * * * *